United States Patent
Zha et al.

(10) Patent No.: US 11,421,113 B2
(45) Date of Patent: Aug. 23, 2022

(54) CHEMICAL PRODUCTS FOR SURFACE PROTECTION

(71) Applicant: Hexion Inc., Columbus, OH (US)

(72) Inventors: Charles Zha, Stafford, TX (US); Jan Beetge, Stafford, TX (US)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 17/072,682

(22) Filed: Oct. 16, 2020

(65) Prior Publication Data

US 2021/0032482 A1 Feb. 4, 2021

Related U.S. Application Data

(62) Division of application No. 15/349,650, filed on Nov. 11, 2016, now Pat. No. 10,836,916.

(60) Provisional application No. 62/260,777, filed on Nov. 30, 2015, provisional application No. 62/258,023, filed on Nov. 20, 2015.

(51) Int. Cl.
| | |
|---|---|
| C09D 5/16 | (2006.01) |
| C02F 5/12 | (2006.01) |
| C07C 233/78 | (2006.01) |
| C07D 233/24 | (2006.01) |
| C02F 103/02 | (2006.01) |
| C02F 103/36 | (2006.01) |

(52) U.S. Cl.
CPC ............ *C09D 5/1625* (2013.01); *C02F 5/12* (2013.01); *C07C 233/78* (2013.01); *C07D 233/24* (2013.01); *C02F 2103/023* (2013.01); *C02F 2103/365* (2013.01); *C02F 2303/20* (2013.01); *C02F 2305/04* (2013.01)

(58) Field of Classification Search
None
See application file for complete search history.

(56) References Cited

FOREIGN PATENT DOCUMENTS

WO WO-2015100031 A1 * 7/2015 ............ C23F 11/149

* cited by examiner

*Primary Examiner* — Katie L. Hammer

(57) ABSTRACT

Some implementations of the present disclosure prevent, reduce or at least slow equipment fouling using passivation as a treatment prior to contacting metallic components with hydrocarbon containing fluid, that is, an environment where fouling occurs. For example, one implementation includes a method of passivating heat exchangers in a SAGD process or system using the compositions and compounds of the present disclosure. The composition may be applied to a component prior to its first inclusion in an online system or following placing the system offline for maintenance. The composition may be used to treat metallic equipment surface(s), for example, via contacting them with a suspension or solution of the composition described herein, prior placing the system online. The method may further include treatment of the process fluid, for example, via injection or batch treatment of the composition with the compositions described herein into the process fluid.

18 Claims, 2 Drawing Sheets

CHEMICAL PRODUCTS FOR SURFACE PROTECTION

RELATED APPLICATION DATA

This application is a divisional application of co-pending U.S. application Ser. No. 15/349,650, with a filing date of Nov. 11, 2016, which application claims benefit to U.S. Provisional Application No. 62/258,023, filed Nov. 20, 2016, and claims benefit to U.S. Provisional Application No. 62/260,777, filed Nov. 30, 2016, of which the entire contents of the applications are incorporated by reference herein.

FIELD

The implementations described herein generally relate to methods and compositions for protecting surfaces, and more particularly to methods and compositions for protecting metal surfaces, clay surfaces, or both in oil production and water treatment processes.

BACKGROUND

In an oil recovery system, such as steam-assisted gravity drainage (SAGD), metal components are often exposed to substances that include hydrocarbons and thus cause fouling of the components. As a specific example, in a SAGD process, hot steam is introduced into the ground via a top injection well. The top well descends down to a deep level below the surface (for example, into oil sands) and then extends horizontally to provide steam to heat oil containing material to a temperature at which it can flow (for example, down via gravity) to a bottom production well. The oil and steam/water mixture is then pumped from a bottom well to the surface where the oil containing mixture may be processed for oil recovery and recycling of the process water.

In processing the oil containing mixture, water is separated from the oil and recycled. The water is recycled partially to minimize environmental impact and partially to conserve resources. The separation process involves the use of metallic heat exchangers to cool the oil containing mixture and separate oil from other process materials. A portion of the water separated from the oil is then recycled (recycled process water).

Components that encounter process water become fouled with a hydrocarbon film that forms on the surface of the components. A common example of such fouling is fouling of a component (for example, heat exchanger) in an SAGD process that is contacted by an oil containing mixture (for example, SAGD process water) derived from the production well. Conventional practice includes taking the system offline, cleaning the heat exchangers, and thereafter placing the system online. Current practice is to clean the heat exchangers in an SAGD system approximately every two weeks. This is time consuming, labor intensive, and expensive.

Another example of heat exchanger fouling is in the crude oil refining process. In addition to the mechanisms that cause heat exchanger fouling in SAGD such as deposit of asphaltene, deposit of inorganic particulates, higher temperature used in refining process also results in coking, polymerization, among others.

It would be desirable if methods and/or compositions could be devised for protecting surfaces, and more particularly to methods and compositions for protecting metal surfaces, clay surfaces, or both in oil production and refining, and water treatment processes.

SUMMARY

The implementations described herein generally relate to methods and compositions for protecting surfaces, and more particularly to methods and compositions for protecting metal surfaces, clay surfaces, or both in oil production and water treatment processes. In one implementation, a composition is provided. The composition comprises at least one compound selected from the following compounds (I-VI) and optionally salts and isomers thereof:

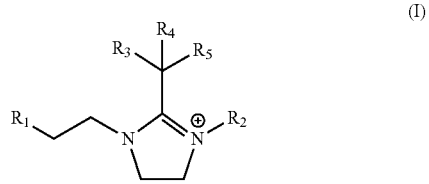
(I)

wherein for Compound (I), $R_1$ is selected from —OH and —$NH_2$, $R_2$ is selected from —H, $C_1$-$C_{18}$ alkyl, $C_1$-$C_{24}$ aminoalkyl, $C_1$-$C_{24}$ alkanoalkyl, —$SO_3^-$, —$CH_2C(O)O^-$, —$P(OH)O_2^-$, and —$CH_2CH_2C(O)OH$, and $R_3$, $R_4$, and $R_5$ are each independently selected from —H, linear or branched $C_1$-$C_{19}$ alkyl groups;

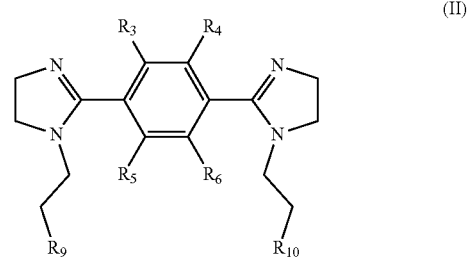
(II)

wherein for Compound (II) $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy, $R_3$, $R_4$, $R_5$, and $R_6$ are each independently selected from —H, $C_1$-$C_4$ alkyl, and $C_1$-$C_4$ alkylcarboxy, and $R_9$ and $R_{10}$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy, —$NHR_1$, —$NHR_2$, —$NHC(O)R_1$, and —$NHC(O)R_2$;

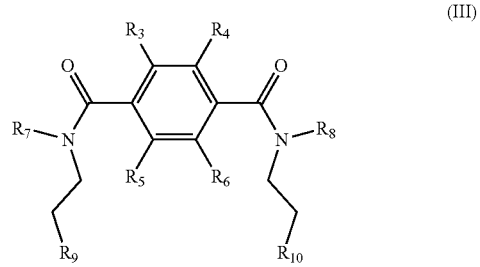
(III)

wherein for Compound (III), $R_9$ is selected from —$NHR_1$, —$NHC(O)R_2$, —$OR_1$, and —$OC(O)R_2$, $R_{10}$ is selected from —NHR$_2$, —NHR$_1$, —NHC(O)R$_2$, —OR$_2$, —OR$_1$, and —OC(O)R$_1$, R$_1$, R$_2$, R$_7$ and R$_8$ are each independently selected from —H, C$_1$-C$_{24}$ alkyl, C$_1$-C$_{24}$ aminoalkyl, C$_1$-C$_{24}$ alkanoalkyl, and C$_1$-C$_{36}$ alkylcarboxy, R$_3$, R$_4$, R$_5$, R$_6$ are each independently selected from —H, C$_1$-C$_4$ alkyl, and C$_1$-C$_4$ alkylcarboxy; and

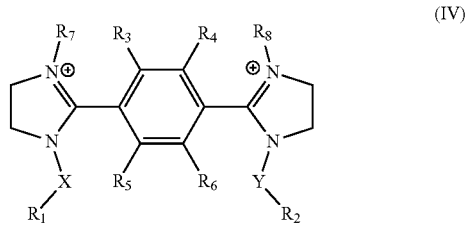

(IV)

for Compound (IV) X and Y are independently an alkylamino group (—R$_{11}$NH—), an alkylamido group (—R$_{11}$NHC(O)—), an alklyether group (—R$_{11}$O—), an alklyester group (—R$_{11}$C(O)O—), or methylene group, wherein R$_{11}$ is a C$_1$-C$_4$ alkyl, R$_1$ and R$_2$ are each independently selected from —H, C$_1$-C$_{24}$ alkyl, C$_1$-C$_{24}$ aminoalkyl, and C$_1$-C$_{24}$ alkanoalkyl, and C$_1$-C$_{36}$ alkylcarboxyl, R$_3$, R$_4$, R$_5$, R$_6$ are each independently selected from —H, —OH, C$_1$-C$_4$ alkyl, and C$_1$-C$_4$ alkylcarboxy, and R$_7$, and R$_8$ are each independently selected from —H, C$_1$-C$_{24}$ alkyl, C$_1$-C$_{24}$ aminoalkyl, C$_1$-C$_{24}$ alkanoalkyl, C$_1$-C$_{36}$ alkylcarboxy, —P(OH)O$_2^-$ and —SO$_3^-$;

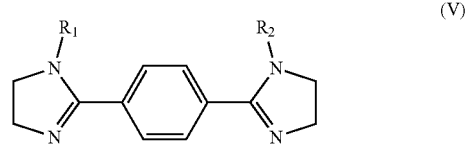

(V)

wherein for Compound (V), R$_1$ and R$_2$ are each independently selected from —H, C$_1$-C$_{24}$ alkyl, C$_1$-C$_{24}$ aminoalkyl, C$_1$-C$_{24}$ alkanoalkyl, and CH$_2$CH$_2$NHR$_3$, R$_3$ is selected from the group of: —H, —C(O)C(R$_4$R$_5$R$_6$), —CH$_2$CH$_2$(OH) CH$_2$OC(O)C(R$_4$R$_5$R$_6$), R$_4$, R$_5$ and R$_6$ are each independently selected from C$_3$-C$_{19}$, —C(O)C(CH$_3$)R$_7$, and —C(O)R$_7$, and R$_7$ is a C$_3$-C$_{19}$ arylalkyl; and In yet another implementation, a method of treating fouling of a metallic component used in an oil recovery system is provided. The method comprises contacting the metallic component with the aforementioned composition and contacting the metallic component with a hydrocarbon-containing process fluid stream.

The features, functions, and advantages that have been discussed can be achieved independently in various implementations or may be combined in yet other implementations, further details of which can be seen with reference to the following description and drawings.

BRIEF DESCRIPTION OF ILLUSTRATIONS

So that the manner in which the above-recited features of the present disclosure can be understood in detail, a more particular description of the disclosure briefly summarized above may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

To facilitate understanding, identical reference numerals have been used, wherever possible, to designate identical elements that are common to the Figures. Additionally, elements of one implementation may be advantageously adapted for utilization in other implementations described herein.

DETAILED DESCRIPTION

Figure 1:
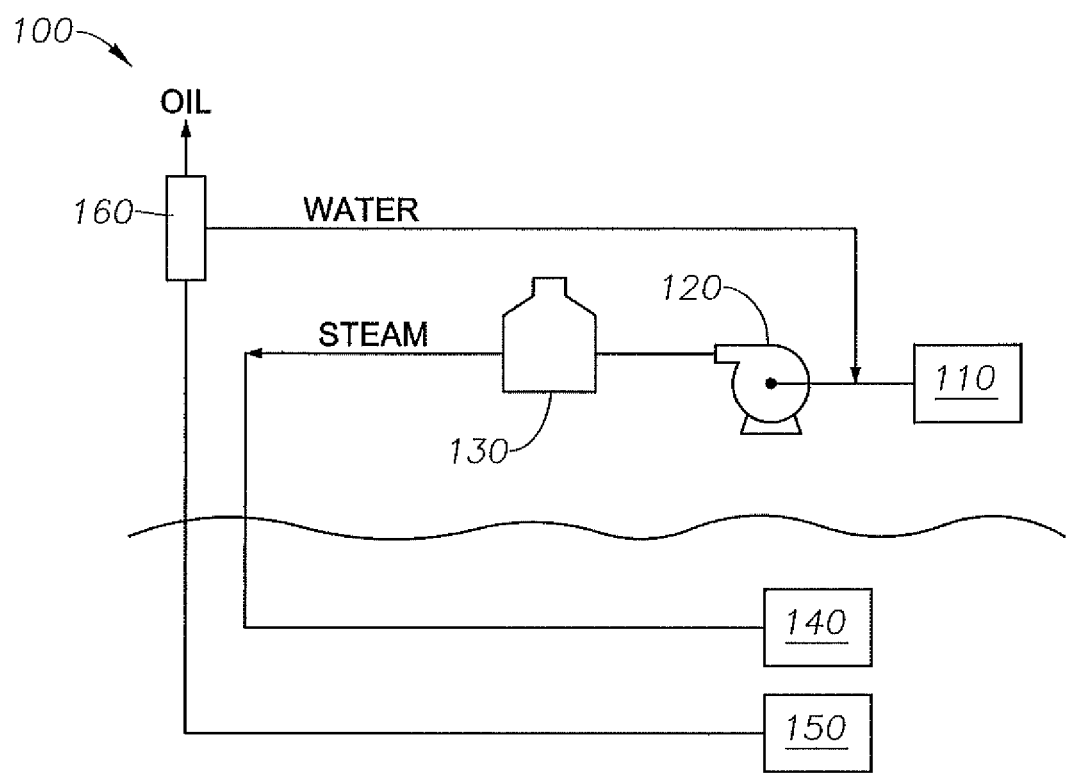
FIG. 1 is a schematic of a production system for steam assisted oil recovery utilizing compositions according to one implementation of the present disclosure.

The following disclosure describes processes and compositions for protecting metal surfaces, clay surfaces, or both in oil production and water treatment processes. Certain details are set forth in the following description and in FIGS. 1-4 to provide a thorough understanding of various implementations of the disclosure. Other details describing well-known compositions, methods and systems often associated with protecting metal surfaces, clay surfaces, or both are not set forth in the following disclosure to avoid unnecessarily obscuring the description of the various implementations.

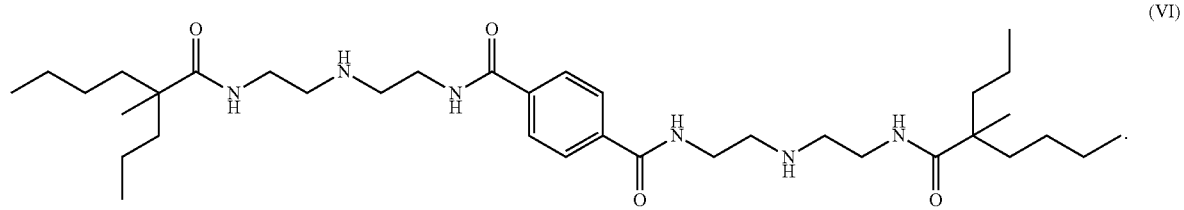 [SMILES: CCCCC(C)(CCC)C(=O)NCCNCCNC(=O)c1ccc(C(=O)NCCNCCNC(=O)C(C)(CCC)CCCC)cc1]

(VI)

Many of the details, components and other features described herein are merely illustrative of particular implementations. Accordingly, other implementations can have other details, components, and features without departing from the spirit or scope of the present disclosure. In addition, further implementations of the disclosure can be practiced without several of the details described below.

As used herein, the following terms have the meaning set forth below unless otherwise stated or clear from the context of their use.

When introducing elements of the present disclosure or exemplary aspects or implementation(s) thereof, the articles "a," "an," "the" and "said" are intended to mean that there are one or more of the elements.

The terms "comprising," "including" and "having" are intended to be inclusive and mean that there may be additional elements other than the listed elements.

The terms "substituent", "radical", "group", "moiety" and "fragment" may be used interchangeably.

The terms "hydroxyl" and "hydroxy" may be used interchangeably.

If a substituent is described as being "optionally substituted," the substituent may be either (1) not substituted or (2) substituted on a substitutable position. If a substitutable position is not substituted, the default substituent is H.

The number of carbon atoms in a substituent can be indicated by the prefix "$C_{A-B}$" where A is the minimum and B is the maximum number of carbon atoms in the substituent.

The symbol "H" denotes a single hydrogen atom and may be used interchangeably with the symbol "—H". "H" may be attached, for example, to an oxygen atom to form a "hydroxy" radical (—OH), or two "H" atoms may be attached to a carbon atom to form a "methylene" (—$CH_2$—) radical.

The term "alkyl" embraces a linear or branched acyclic alkyl radical containing from 1 to about 24 carbon atoms. In some embodiments, alkyl is a $C_{1-24}$ alkyl, $C_{1-20}$ alkyl, $C_{1-18}$ alkyl $C_{1-10}$ alkyl, $C_{1-6}$ alkyl or $C_{1-3}$ alkyl radical. Examples of alkyl include, but are not limited to, methyl, ethyl, propyl, isopropyl, butyl, isobutyl, tert-butyl, sec-butyl, pentan-3-yl

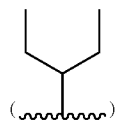 [SMILES: *C(CC)CC]

and the like.

The term "aminoalkyl" embraces an amino radical attached to a parent molecular scaffold through an alkyl radical (for example, $NH_2$-alkyl-scaffold).

The term "alkylcarboxy" embraces the COOR group, where R is alkyl or substituted alkyl.

The term "aryl" refers to any monocyclic, bicyclic or tricyclic cyclized carbon radical, wherein at least one ring is aromatic. An aromatic radical may be fused to a non-aromatic cycloalkyl or heterocyclyl radical. Examples of aryl include phenyl and naphthyl.

The term "arylalkyl" embraces aryl attached to a parent molecular scaffold through alkyl. Examples of arylalkyl include benzyl, diphenylmethyl, triphenylmethyl, phenylethyl and diphenylethyl. The terms "benzyl" and "phenylmethyl" may be used interchangeably.

All percentages, preferred amounts or measurements, ranges and endpoints thereof herein are inclusive, that is, "less than about 10" includes about 10. "At least" is, thus, equivalent to "greater than or equal to," and "at most" is, thus, equivalent "to less than or equal to." Numbers herein have no more precision than stated. Thus, "105" includes at least from 104.5 to 105.49. Furthermore, all lists are inclusive of combinations of two or more members of the list. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus, a range that has an advantageous lower limit combined with a most preferred upper limit is preferred for the practice of the implementations described herein. All amounts, ratios, proportions and other measurements are by weight unless stated otherwise. All percentages refer to weight percent based on total composition according to the practice of the present disclosure unless stated otherwise.

There are several significant risks in the storage, transport, handling and processing of complex and even mildly corrosive fluids such as crude oil. The transport and processing of fluids such as crude oil can be significantly impacted by deposition of sub-fractions of the complex fluid on the surfaces of pipelines and equipment to reduce flow or interfere with fluid processing operations such as heat transfer in heat exchangers. Deposition of inorganic scale, asphaltene, and paraffin precipitation are typical examples of such surface deposition. Cleaning, repair or replacement of pipelines and equipment can be very costly and disruptive. In more extreme cases, this surface deposition can compromise asset integrity leading to possible system failure, which may have a significant negative impact on environmental, health, and safety aspects of any operation.

Currently, corrosion inhibitors based-on amides and imidazolines are often used in formulations of process additives to improve and insure flow and processing of multicomponent fluids. Surfactants based on phosphate esters, quaternary amines, polysulfonates and various nonionic polymers have also been used as additives to ensure flow and processing of fluids. These current products form a protective film or a "passivation film" on the metal surface. This protective film prevents water and other corrosion factors from contacting the metal surface. However, these protective films formed using currently available corrosion inhibitors often suffer from defects in harsh conditions such as high temperature and high flow rate environments. Currently available corrosion inhibitors also typically require application in high concentrations.

Another issue related to the production and transportation of heavy oil production is the deposition of asphaltene and other organic and inorganic components in bitumen on the heat exchangers and other equipment. More specifically is the fouling in heat exchangers in SAGD operations in Alberta, Canada. The fouling on the heat exchanger in SAGD operations is so bad that the operation is interrupted every one to two weeks to clean the heat exchangers. The costly cleaning operation and the production loss due to the interruption have significant negative impacts on the costs of the SAGD operation. No commercial product has been reported that can effectively mitigate this issue.

Conventional attempts to deal with the fouling problem have been ineffective and result in the taking the system offline to clean components, for example, heat exchangers, on a regular basis. For example, current practice is to clean heat exchangers in an SAGD system approximately every two weeks.

Implementations of the present disclosure include novel compositions based on novel compounds that overcome the aforementioned deficiencies of currently available corrosion inhibitors. The compositions of the present disclosure may be used in various applications including, but not limited to, the protection or passivation of metal surfaces, clay surfaces, or both. Typical applications of the compositions of the present disclosure, when used alone or formulated with other components, include use as antifouling agents, passivation agents, shale inhibitors, corrosion inhibitors, scale inhibitors in oil production, paraffin inhibitors, water treatment, and hydrate inhibitors.

In some implementations of the present disclosure, the compositions and compounds of the present disclosure are designed to be surface active with strong interactions with metal surfaces, clay surfaces, or both. The compositions and compounds of the present disclosure partition and adhere to metal or clay surfaces to form a barrier layer or film with exceptional persistence against mechanical damage, thermal dissolution, or both. This barrier layer efficiently prevents, reduces or at least slows deposition on the metal or clay surface. The barrier layer also efficiently prevents, reduces, or at least slows chemical reaction with the metal or clay surface, or both. In some implementations, surface protection is accomplished by continuous injection of the composition into the process fluid where the composition will partition to the metal surface, the clay surface, or both. In some implementations, surface protection is accomplished by batch treatment of the process fluid. In some implementations, the compositions of the present disclosure are designed to adhere to clay surfaces forming a water-repelling barrier to protect downhole formations from erosion. In some implementations, the compositions of the present disclosure are functional at high temperatures (for example, temperatures up to 350 degrees Celsius) and effective in low application concentrations (for example, about 100 ppm or less).

Some implementations of the present disclosure prevent, reduce or at least slow equipment fouling using passivation as a treatment prior to contacting metallic components with hydrocarbon containing fluid, that is, an environment where fouling occurs. For example, one implementation includes a method of passivating heat exchangers, such as in a SAGD process, or systems using the compositions and compounds of the present disclosure. The composition may be applied to a component prior to its first inclusion in an online system or following placing the system offline for maintenance. The composition may be used to treat metallic equipment surface(s), for example, via contacting them with a suspension or solution of the composition described herein, prior placing the system online. The method may further include treatment of the process fluid, for example, via injection or batch treatment of the composition with the compositions described herein into the process fluid.

The composition of the present disclosure may be applied in a variety of ways. In one example, the composition described herein can be applied in batch treatments or continuously injected into the process fluid during operation.

Another implementation described herein includes, in addition to or as an alternative to treatment prior to placing the system online, a process of continuously, periodically, or intermittently providing the composition to an ongoing process, for example, via introduction of the composition of the present disclosure into the process flow (for example, into an online SAGD process flow) such that the metallic surface(s) are exposed to the composition on a continuous, periodic or intermittent basis.

Another implementation of the present disclosure includes adding a maintenance dose of the composition of the present disclosure to the process fluid alone or in combination with other treatment, for example, after component or equipment cleaning. Inclusion of a maintenance dose of the composition of the present disclosure provides an added benefit of preventing corrosion in other system components that have not been treated or treated after cleaning, such as piping, even if fouling is not of primary concern.

Another implementation of the present disclosure includes using the composition, alone or in combination with additional compounds, in the cleaning product used in the cleaning liquid used in a mechanical/chemical cleaning process which could be agitation, pumping, ultrasonic baths, and other devices.

In some implementations of the present disclosure, the compositions described herein serve as corrosion inhibitors with improved performance relative to current commercial products.

In some implementations of the present disclosure, the compositions described herein serve as scale inhibitors in oil and gas production since they are able to reduce the surface energy of metals resulting in reduced deposits.

In some implementations of the present disclosure, the compositions described herein serve as shale inhibitors in oil and gas production due to their strong adhesion with clay surfaces and their strong water repelling hydrophobic tails.

In some implementations of the present disclosure, the compositions described herein serve as hydrate inhibitors in oil and gas production due to their strong adhesion with clathrate hydrates and their strong water repelling hydrophobic tails that block the agglomeration of the hydrates.

The compositions of the present disclosure work at low concentrations, for example, about 1,000 ppm or less in continuous injection operation (for example, about 500 ppm or less, about 100 ppm or less, about 75 ppm or less; about 50 ppm or less; about 25 ppm or less; from about 1 ppm to about 1000; from about 1 ppm to about 750; from about 5 ppm to about 750; ppm from about 1 ppm to about 500; ppm from about 1 ppm to about 100 ppm; from about 5 ppm to about 75 ppm; from about 5 ppm to about 50 ppm; or from about 5 ppm to about 25 ppm). For antifouling application in SAGD, the cost of chemical injection will offset the much higher cost associated with manual cleaning and loss in productivity. Further, residual composition in the system will also benefit downstream processes in other operational areas, such as corrosion protection and scale inhibition in the rest of the equipment and pipelines.

FIG. 1 is a schematic of an exemplary production system 100 for steam assisted oil recovery utilizing compositions according to implementations of the present disclosure. The exemplary production system 100 includes a boiler feed antifouling composition injector 110, a pump 120, a steam generator 130, such as a once-through steam generator (OTSG), an injection well 140, a production well 150, and a separator 160. While illustrated in an exemplary SAGD configuration, other techniques, such as cyclic steam stimulation, solvent assisted SAGD, or steam drive, may employ the steam generated as described herein. The injection well 140 may extend in a horizontal direction and the production well 150 may also extend in the horizontal direction.

In operation, the steam enters the formation along the injection well 140 forming a steam chamber with heat transferred from the steam to the oil or bitumen in the formation. The oil once heated becomes less viscous and mobile enough for flowing by gravity along with condensate of the steam to the production well 150. A mixture of the condensate and oil collected in the production well 150 flows to the surface where the oil is removed in the separator 160 from the condensate, which may be recycled for generating additional steam to sustain steam injection.

The water that is recycled even with treatment contains dissolved organic compounds believed to contribute to fouling in the steam generator 130. For example, phenolic compounds and other oxygenated hydrocarbons in the water may couple and/or polymerize under conditions in the steam generator 130. Any of these polymerized compounds that drop out of solution may foul the steam generator 130 and may undergo coking reactions further contributing to deposition in the steam generator 130. The antifouling composition injector 110 therefore adds the composition of the present disclosure to the water prior to the water entering the steam generator 130.

While the invention described herein is describe with reference to an oil recovery system, the inventive composition and process can be used in other applications, such as in an oil refining system to address fouling of components.

Composition:

While the compound structures are described below having preferred substitute positions, the invention contemplates isomers of the compound structures, such as compound structures having isomers of ortho (o), meta (m) and/or para (p) positions for one or more substituents.

In one implementation, the composition comprises the reaction products of at least one of: (a) terephthalic acid, (b) a neo-acid having the structure $(R_1R_2R_3)$—C—COOH, wherein $R_1$, $R_2$ and $R_3$ are each independently selected from linear or branched alkyl groups, the neo-acid may be a $C_5$-$C_{22}$ neoacid, such as a such as a $C_5$-$C_{19}$ neoacid, for example, a $C_5$-$C_{10}$ neoacid, with $R_1$+$R_2$+$R_3$ having a combined 3 to 20 carbon atoms for a $C_5$-$C_{22}$ neoacid, $R_1$+$R_2$+$R_3$ having a combined 3 to 17 carbon atoms $C_5$-$C_{19}$ neoacid, $R_1$+$R_2$+$R_3$ having a combined 3 to 8 carbon atoms and $C_5$-$C_{10}$ neoacid, (c) acrylic acid, (d) diethylenetriamine, (e) rosin, (f) tall oil fatty acids, $C_{12}$-$C_{24}$ fatty acids, and other fatty acids, and (g) a glycidyl ester of a neo-acid. In one implementation, a mixture of one or more $C_5$-$C_{22}$ neo-acids, for example, a mixture of $C_{10}$-$C_{19}$ neo-acids or a mixture of $C_9$-$C_{13}$ neo-acids, may be used for the $C_5$-$C_{22}$ neo-acid described herein.

In another implementation, a composition comprising at least one of the following structures of Compounds (I)-(VI), isomers thereof, and mixtures thereof is provided.

In some implementations, the composition of the present disclosure comprise a generic formula and optionally salts and isomers thereof as defined by the structure of Compound (I):

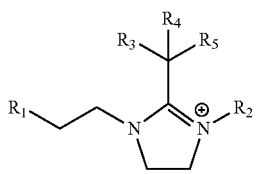
(I)

In Compound (I), $R_1$ is selected from —OH and —NH$_2$, $R_2$ is selected from —H, $C_1$-$C_{18}$ alkyl, $C_1$-$C_{24}$ aminoalkyl, $C_1$-$C_{24}$ alkanoalkyl, —P(OH)O$_2^-$, —CH$_2$C(O)O$^-$, and —CH$_2$CH$_2$C(O)OH, and $R_3$, $R_4$, and $R_5$ are each independently selected from —H, linear $C_1$-$C_{19}$ alkyl groups or branched $C_1$-$C_{19}$ alkyl groups.

In some implementations, Compound (I) is defined by the following structure and optionally salts and isomers thereof:

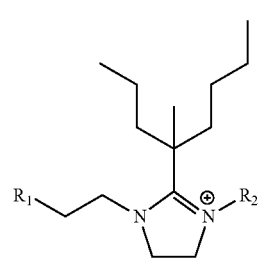
(I-A)

In Compound (I-A), $R_1$ is selected from —OH and —NH$_2$ and $R_2$ is selected from —H, $C_1$-$C_{18}$ alkyl, $C_1$-$C_{24}$ aminoalkyl, $C_1$-$C_{24}$ alkanoalkyl, —SO$_3^-$, —CH$_2$C(O)O$^-$, —P(OH)O$_2^-$ and —CH$_2$CH$_2$C(O)OH.

In some implementations, Compound (I) is defined by the following structure and optionally salts and isomers thereof:

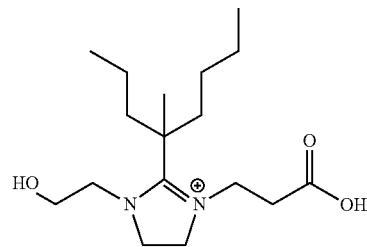
(I-B)

In some implementations, Compound (I) is defined by the following structure and optionally salts and isomers thereof:

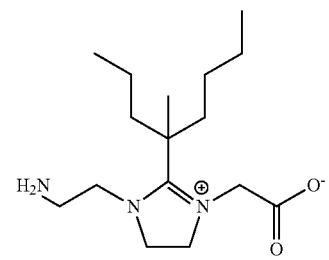
(I-C)

In some implementations, Compound (I) is defined by the following structure and optionally salts and isomers thereof:

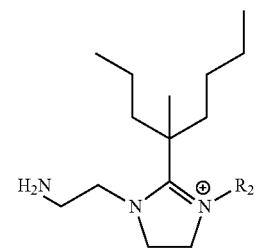
(I-D)

In Compound (I-D) $R_2$ is selected from —H, $C_1$-$C_{18}$ alkyl, $C_1$-$C_{24}$ aminoalkyl, $C_1$-$C_{24}$ alkanoalkyl, —SO$_3^-$, —CH$_2$C(O)O$^-$, —P(OH)O$_2^-$ and —CH$_2$CH$_2$C(O)OH.

In some implementations, Compound (I) is defined by the following structure and optionally salts and isomers thereof:

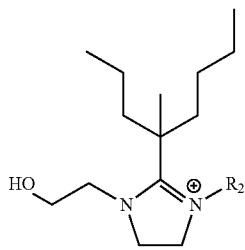

(I-E)

In Compound (I-E) $R_2$ is selected from H, $C_1$-$C_{18}$ alkyl, $C_1$-$C_{24}$ aminoalkyl, $C_1$-$C_{24}$ alkanoalkyl, —$CH_2C(O)O^-$, —$P(OH)O_2^-$ and —$CH_2CH_2C(O)OH$.

In some implementations, Compound (I) is defined by the following structure and optionally salts and isomers thereof:

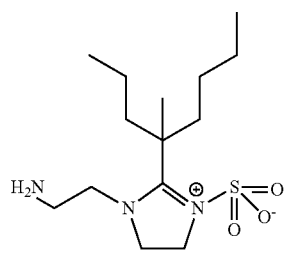

(I-F)

In some implementations, Compound (I) is defined by the following structure and optionally salts and isomers thereof:

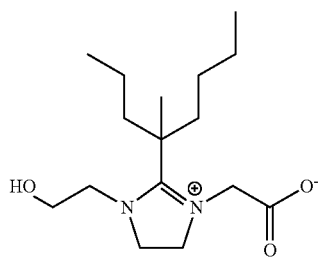

(I-G)

In some implementations, the composition of Compound (I) is defined by the following structure and optionally salts and isomers thereof:

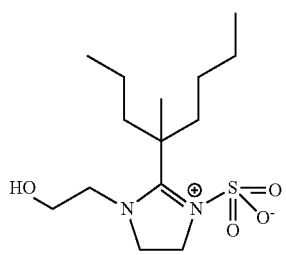

(I-H)

In some implementations, the composition of Compound (I) is defined by the following structure and optionally salts and isomers thereof:

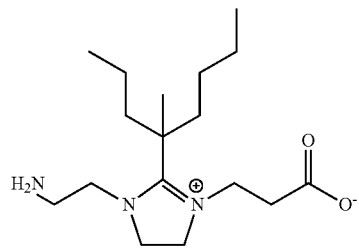

(I-I)

In some implementations, the composition of Compound (I) is defined by the following structure and optionally salts and isomers thereof:

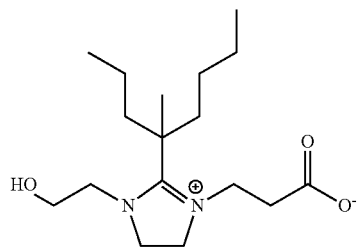

(I-J)

In some implementations, the composition of the present disclosure comprise a generic formula and optionally salts and isomers thereof as defined by the structure of Compound (II):

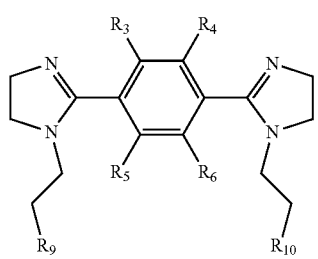

(II)

In Compound (II), $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compound (II), $R_3$, $R_4$, $R_5$, and $R_6$ are each independently selected from —H, $C_1$-$C_4$ alkyl, and $C_1$-$C_4$ alkylcarboxy. In Compound (II), $R_9$ and $R_{10}$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy, —$NHR_1$, —$NHR_2$, —$NHC(O)R_1$, and —$NHC(O)R_2$.

In some implementations, Compound (II) is defined the structures of Compounds (II-A), (II-B), and (II-C) and optionally salts and isomers thereof:

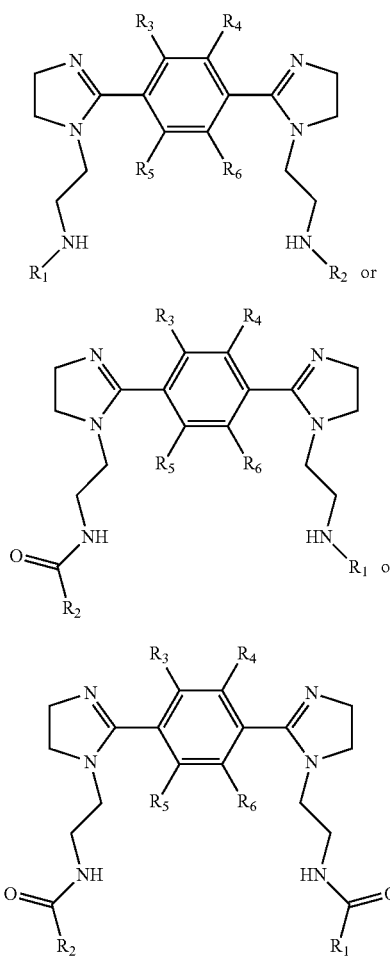

(II-A)

(II-B)

(II-C)

In Compound (II-A), (II-B), and (II-C), $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compound (II-A), (II-B), and (II-C), $R_3$, $R_4$, $R_5$, and $R_6$ are each independently selected from —H, $C_1$-$C_4$ alkyl, and $C_1$-$C_4$ alkylcarboxy.

In some implementations, the composition of the present disclosure comprises a generic formula and optionally salts and isomers thereof as defined by the structure of Compound (III):

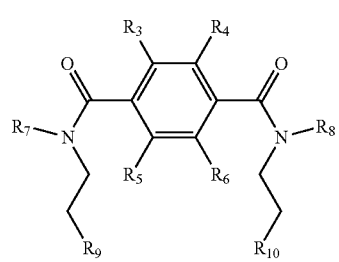

(III)

In Compound (III), $R_9$ is selected from —$NHR_1$, —$NHC(O)R_2$, —$OR_1$, and —$OC(O)R_2$. In Compound (III), $R_{10}$ is selected from —$NHR_2$, —$NHR_1$, —$NHC(O)R_2$, —$OR_2$, —$OR_1$, and —$OC(O)R_1$. In Compound (III), $R_1$, $R_2$, $R_7$ and $R_8$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compound (III), $R_3$, $R_4$, $R_5$, $R_6$ are each independently selected from —H, $C_1$-$C_4$ alkyl, and $C_1$-$C_4$ alkylcarboxy.

In some implementations, Compound (III) is defined by the structure of Compounds (III-A), (III-B), (III-C), (III-D), (III-E) and (III-F) and optionally salts and isomers thereof:

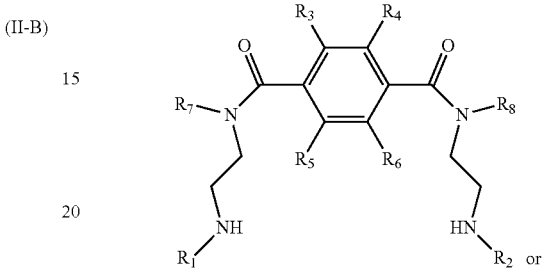

(III-A)

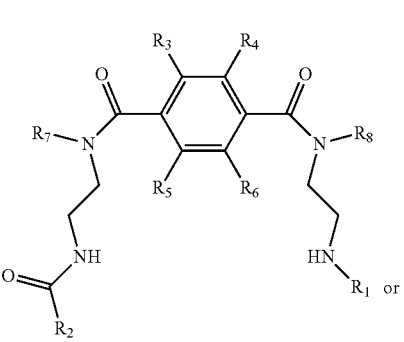

(III-B)

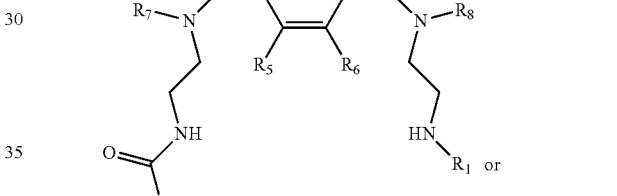

(III-C)

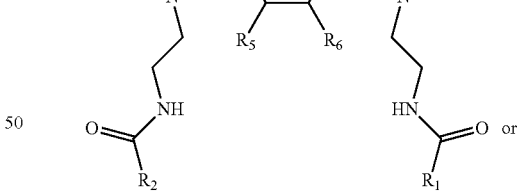

(III-D)

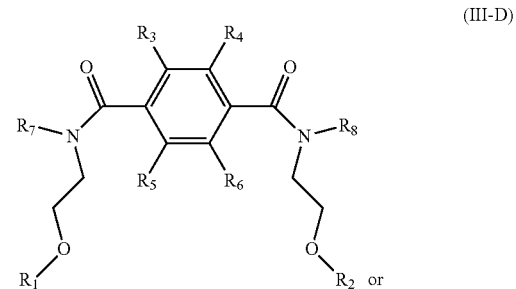

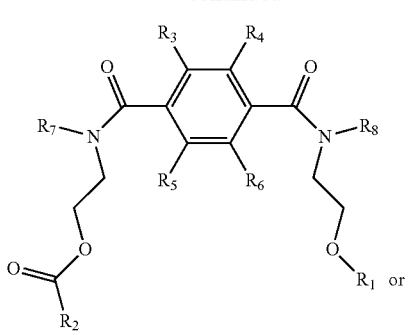

(III-E)

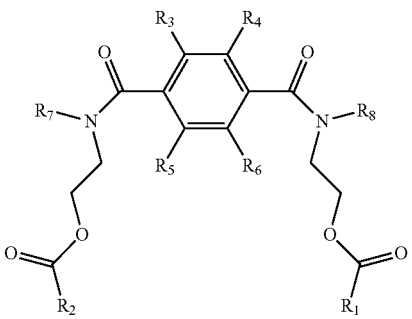

(III-F)

In Compounds (III-A), (III-B), (III-C), (III-D), (III-E), and (III-F), $R_1$, $R_2$, $R_7$ and $R_8$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compounds (III-A), (III-B), (III-C), (III-D), (III-E), and (III-F), $R_3$, $R_4$, $R_5$, $R_6$ are each independently selected from —H, $C_1$-$C_4$ alkyl, and $C_1$-$C_4$ alkylcarboxy.

In some implementations, the composition of the present disclosure comprises a generic formula and optionally salts and isomers thereof as defined by the structure of Compound (IV):

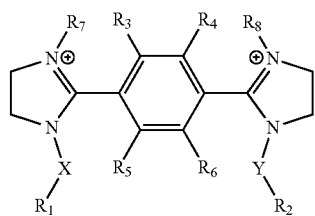

(IV)

In Compound (IV) X and Y are independently an alkylamino group (—$R_{11}$NH—), an alkylamido group (—$R_{11}$NHC(O)—), an alkylether group (—$R_{11}$O—), an alkylester group (—$R_{11}$C(O)O—), or methylene group, wherein $R_{11}$ is a $C_1$-$C_4$ alkyl (for example, $CH_2$, $C_2H_4$, $C_3H_6$, $C_4H_8$). Each of the aforementioned groups may be substituted with amino groups, hydroxyl groups, ester groups, and combinations thereof. For example, suitable substituted groups include aminoalkyl esters, amino hydroxyl alkyl esters, alkoxy alkyl esters, and alkoxy hydroxyl alkyl esters. In some implementations, X and Y are independently selected from —$CH_2CH_2NH$—, —$CH_2CH_2O$—, —$CH_2CH_2NHC(O)$—, —$CH_2CH_2OC(O)$—, —$CH_2CH_2NHCH_2CH(OH)CH_2OC(O)$—, —$CH_2CH_2NHCH_2CH(OH)CH_2OC(O)$—, —$CH_2CH_2OCH_2CH(OH)CH_2OC(O)$—, and —$CH_2CH_2OCH_2CH(OH)CH_2OC(O)$—.

In Compound (IV), $R_1$ and $R_2$ are each independently selected from —H, $C_1$-$C_{24}$ alkyl, $C_1$-$C_{24}$ aminoalkyl, and $C_1$-$C_{24}$ alkanoalkyl, and $C_1$-$C_{36}$ alkylcarboxyl.

In Compound (IV), $R_3$, $R_4$, $R_5$, $R_6$ are each independently selected from —H, —OH, $C_1$-$C_4$ alkyl, and $C_1$-$C_4$ alkylcarboxy.

In Compound (IV), $R_7$, and $R_8$ are each independently selected from —H, $C_1$-$C_{24}$ alkyl, $C_1$-$C_{24}$ aminoalkyl, $C_1$-$C_{24}$ alkanoalkyl, $C_1$-$C_{36}$ alkylcarboxy, $C_1$-$C_{20}$ arylalkyl such as benzyl group, —P(OH)$O_2^-$ and —$SO_3^-$. In some implementations, $R_7$, and $R_8$ are each independently selected from —$CH_2C(O)O^-$, —$CH_2CH_2C(O)O^-$, —P(OH)$O_2^-$ and —$SO_3^-$.

In some implementations, Compound (IV) is defined by the structure of Compound (IV-A) and optionally salts and isomers thereof:

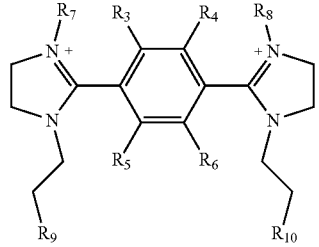

(IV-A)

In Compound (IV-A), $R_3$, $R_4$, $R_5$, $R_6$ are each independently selected from —H, —OH, $C_1$-$C_4$ alkyl, and $C_1$-$C_4$ alkylcarboxy. In Compound (IV-A), $R_9$ and $R_{10}$ are each independently selected from —$NHR_1$, —$NHR_2$, —NHC(O)$R_1$, —NHC(O)$R_2$, —$OR_1$, —$OR_2$, —OC(O)$R_1$, and —OC(O)$R_2$. In Compound (IV-A), $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compound (IV-A), $R_7$ and $R_8$ are each independently selected from —$CH_2C(O)O^-$, —$CH_2CH_2C(O)O^-$, —P(OH)$O_2^-$, —$SO_3^-$ and $C_7$-$C_{20}$ arylalkyl such as benzyl group.

In some implementations, Compound (IV-A) is defined by the structures of Compounds (IV-A-1), (IV-A-2), (IV-A-3), (IV-A-4), (IV-A-5), (IV-A-6), (IV-A-7), (IV-A-8), (IV-A-9), (IV-A-10), (IV-A-11), and (IV-A-12) and optionally salts and isomers thereof:

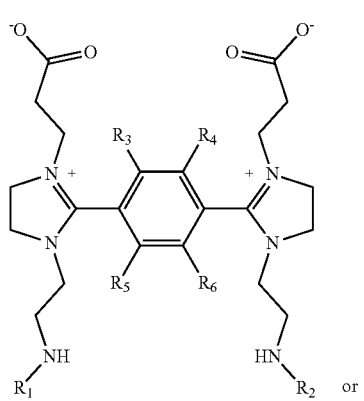

(IV-A-1)

or

-continued
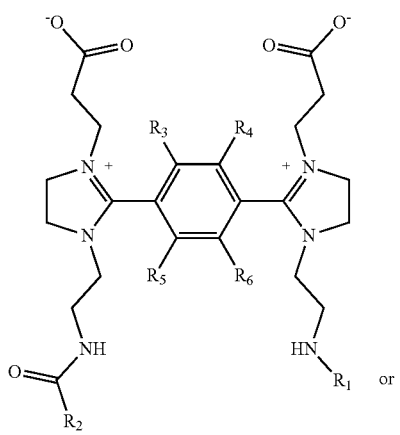
(IV-A-2)
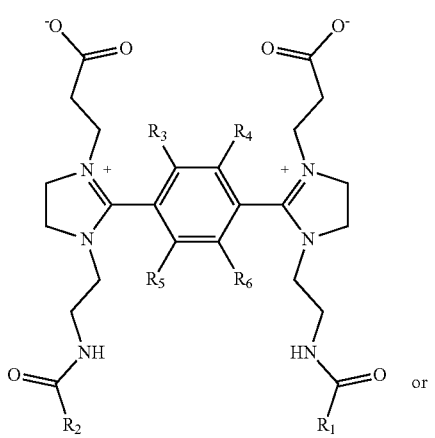
(IV-A-3)
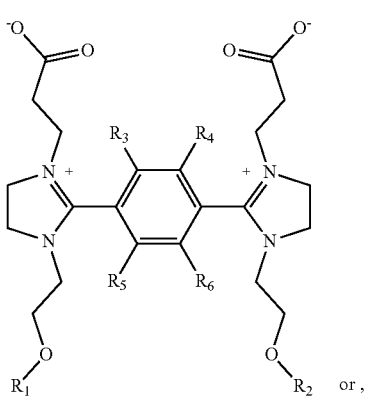
(IV-A-4)
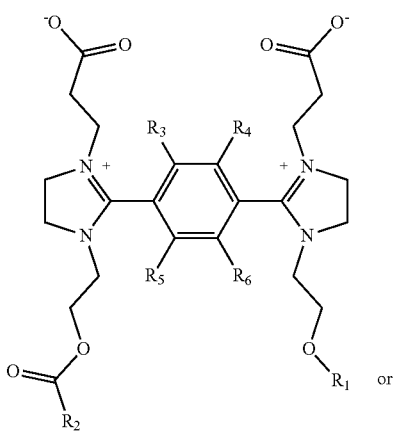
(IV-A-5)
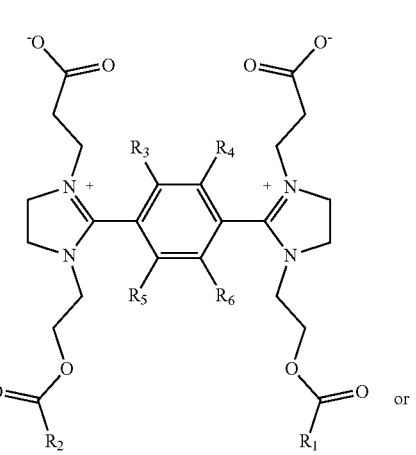
(IV-A-6)
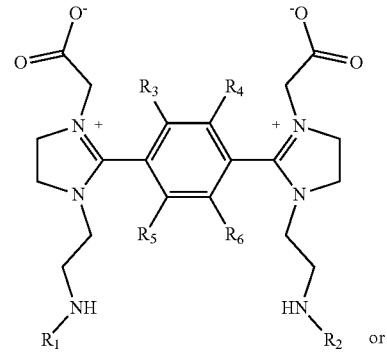
(IV-A-7)
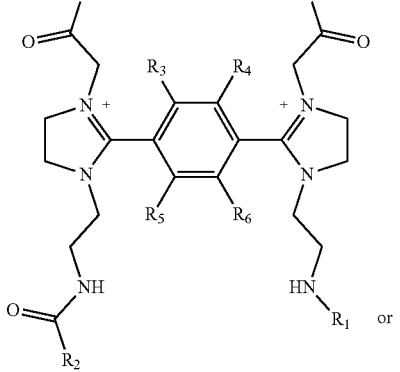
(IV-A-8)

-continued

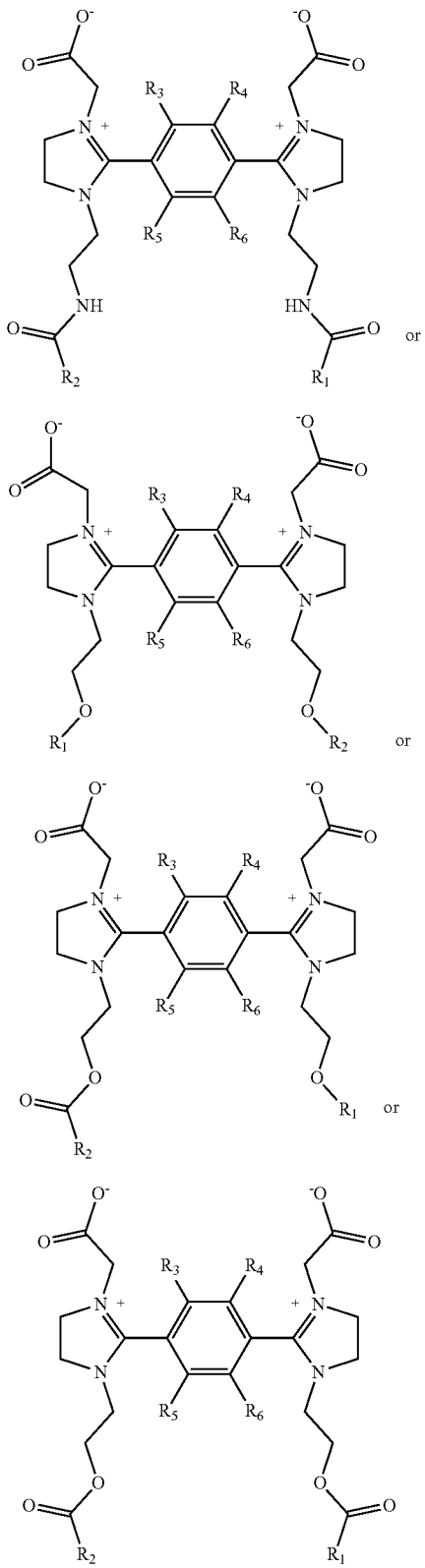

(IV-A-9)

(IV-A-10)

(IV-A-11)

(IV-A-12)

In Compounds (IV-A-1), (IV-A-2), (IV-A-3), (IV-A-4), (IV-A-5), (IV-A-6), (IV-A-7), (IV-A-8), (IV-A-9), (IV-A-10), (IV-A-11), and (IV-A-12), $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy. In Compounds (IV-A-1), (IV-A-2), (IV-A-3), (IV-A-4), (IV-A-5), (IV-A-6), (IV-A-7), (IV-A-8), (IV-A-9), (IV-A-10), (IV-A-11), and (IV-A-12), $R_3$, $R_4$, $R_5$, $R_6$ are each independently selected from —H, —OH, $C_1$-$C_4$ alkyl, and $C_1$-$C_4$ alkylcarboxy.

In some implementations, Compound (IV) is defined by the structure of Compound (IV-B) and optionally salts and isomers thereof:

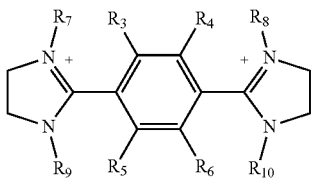

(IV-B)

In Compound (IV-B), $R_1$ and $R_2$ are each independently selected from H, $C_1$-$C_{24}$ alkyl, $C_1$-$C_{24}$ aminoalkyl, and $C_1$-$C_{24}$ alkanoalkyl. In Compound (IV-B), $R_3$, $R_4$, $R_5$, $R_6$ are each independently selected from —H, —OH, $C_1$-$C_4$ alkyl, and $C_1$-$C_4$ alkylcarboxy. In Compound (IV-B), $R_9$ and $R_{10}$ are each independently selected from —CH$_2$CH$_2$NHCH$_2$CH(OH)CH$_2$OC(O)R$_1$, —CH$_2$CH$_2$NHCH$_2$CH(OH)CH$_2$OC(O)R$_2$, —CH$_2$CH$_2$OCH$_2$CH(OH)CH$_2$OC(O)R$_1$, —CH$_2$CH$_2$OCH$_2$CH(OH)CH$_2$OC(O)R$_2$, and

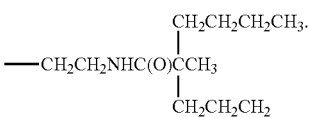

In Compound (IV-B), $R_7$ and $R_8$ are each independently selected from —CH$_2$C(O)O$^-$, —CH$_2$CH$_2$C(O)O$^-$, —P(OH)O$_2^-$, —SO$_3^-$ and $C_7$-$C_{20}$ arylalkyl such as benzyl group.

In some implementations, Compound (IV-B) is defined by the structure of Compounds (IV-B-1), (IV-B-2), (IV-B-3), (IV-B-4), and (IV-B-5) and optionally salts and isomers thereof:

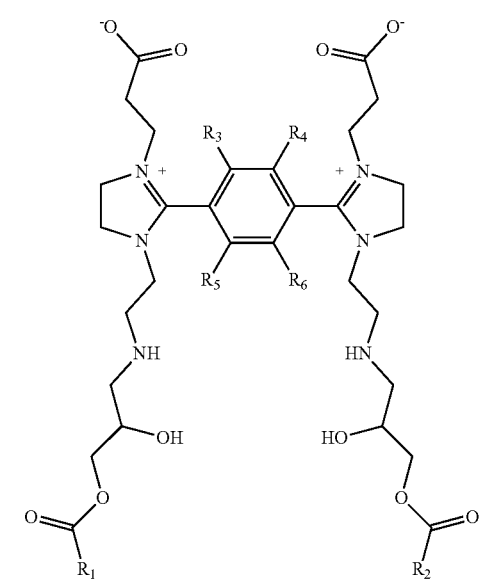

(IV-B-1)

or

-continued (IV-B-2)

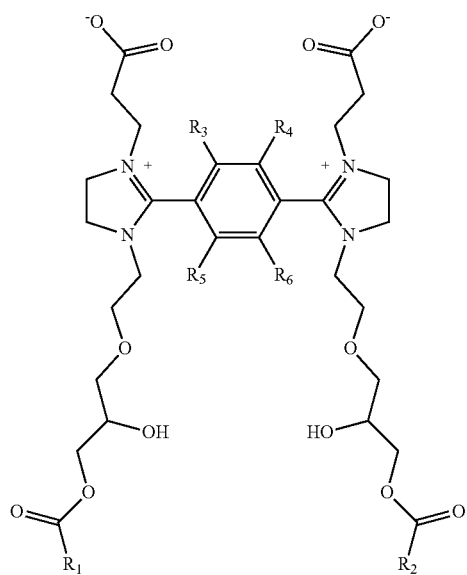

or (IV-B-3)

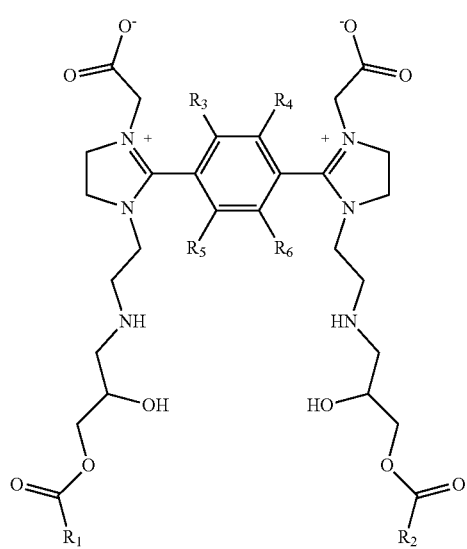

or (IV-B-4)

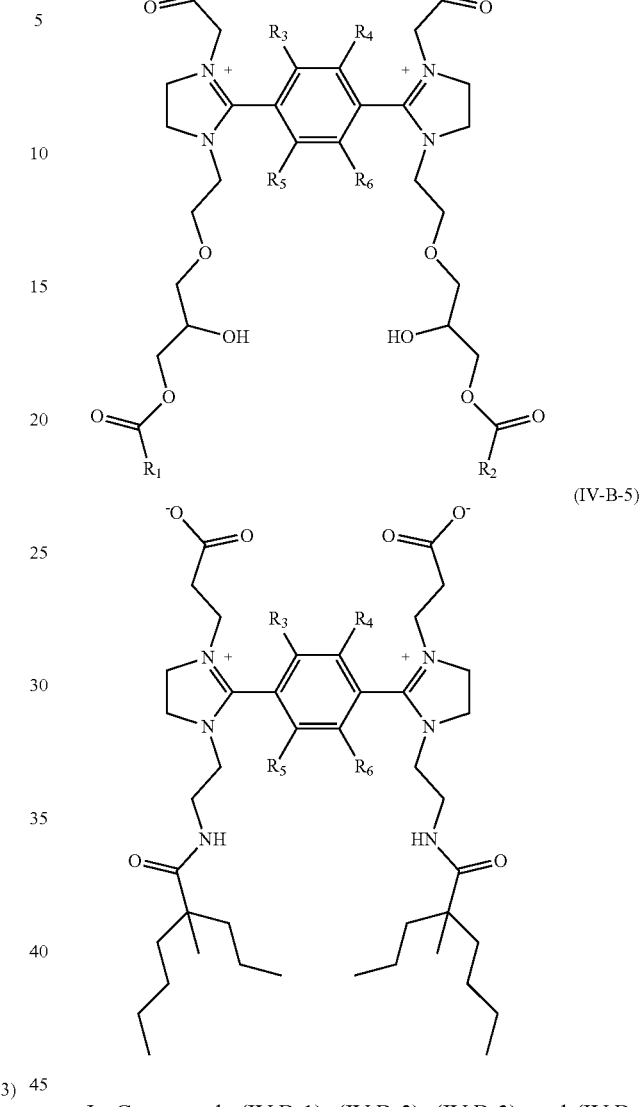

In Compounds (IV-B-1), (IV-B-2), (IV-B-3), and (IV-B-4), $R_1$ and $R_2$ are each independently selected from $C_1$-$C_{20}$ alkyl, $C_1$-$C_{20}$ aminoalkyl, and $C_1$-$C_{20}$ alkanoalkyl. In Compounds (IV-B-1), (IV-B-2), (IV-B-3), (IV-B-4), and (IV-B-5), $R_3$, $R_4$, $R_5$, $R_6$ are each independently selected from —H, —OH, $C_1$-$C_4$ alkyl, and $C_1$-$C_4$ alkylcarboxy.

In some implementations, Compound (IV) is defined by the structure of Compound (IV-C) and optionally salts and isomers thereof:

(IV-C)

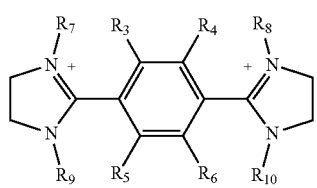

In Compound (IV-C), $R_1$, $R_2$, $R_7$, and $R_8$ are each independently selected from —H, $C_1$-$C_{24}$ alkyl, $C_1$-$C_{24}$ aminoalkyl, $C_1$-$C_{24}$ alkanoalkyl, $C_1$-$C_{36}$ alkylcarboxy, —P(OH)$O_2^-$, —$SO_3^-$ and $C_7$-$C_{20}$ arylalkyl such as benzyl group. In Compound (IV-C), $R_3$, $R_4$, $R_5$, $R_6$ are each independently selected from —H, —OH, $C_1$-$C_4$ alkyl, and $C_1$-$C_4$ alkylcarboxy. In Compound (IV-C), $R_9$ and $R_{10}$ are each independently selected from —$CH_2CH_2NHR_1$, —$CH_2CH_2NHR_2$, —$CH_2CH_2NHC(O)R_1$, —$CH_2CH_2NHC(O)R_2$, —$CH_2CH_2OR_1$, —$CH_2CH_2OR_2$, —$CH_2CH_2OC(O)R_1$, and —$CH_2CH_2OC(O)R_2$.

In some implementations, Compound (IV-C) is defined by the structures of Compounds (IV-C-1), (IV-C-2), (IV-C-3), (IV-C-4), (IV-C-5) and (IV-C-6) and optionally salts and isomers thereof:

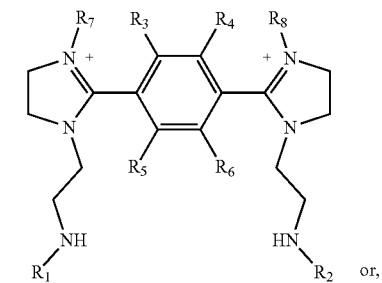

(IV-C-1)

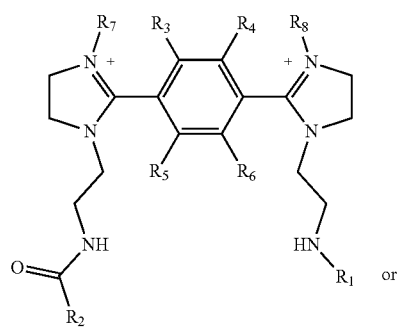

(IV-C-2)

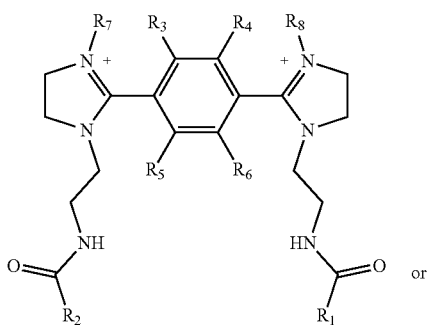

(IV-C-3)

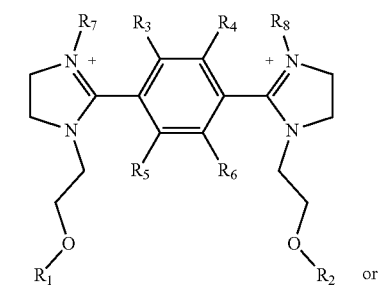

(IV-C-4)

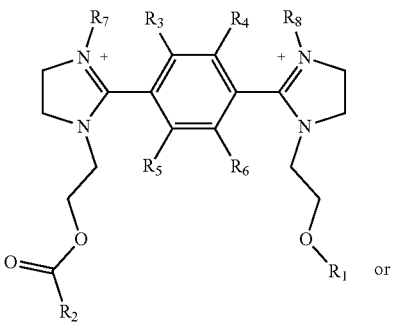

(IV-C-5)

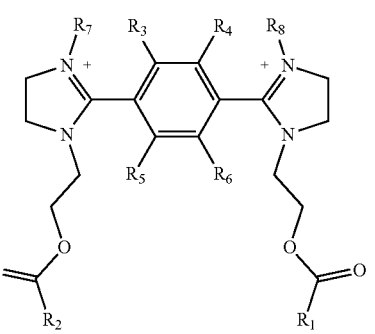

(IV-C-6)

In Compounds (IV-C-1), (IV-C-2), (IV-C-3), (IV-C-4), (IV-C-5) and (IV-C-6), $R_1$, $R_2$, $R_7$, and $R_8$ are each independently selected from —H, $C_1$-$C_{24}$ alkyl, $C_1$-$C_{24}$ aminoalkyl, $C_1$-$C_{24}$ alkanoalkyl, $C_1$-$C_{36}$ alkylcarboxy, —P(OH)$O_2^-$, —$SO_3^-$ and $C_7$-$C_{20}$ arylalkyl such as benzyl group. In Compounds (IV-C-1), (IV-C-2), (IV-C-3), (IV-C-4), (IV-C-5) and (IV-C-6), $R_3$, $R_4$, $R_5$, $R_6$ are each independently selected from —H, —OH, $C_1$-$C_4$ alkyl, and $C_1$-$C_4$ alkylcarboxy.

In some implementations, Compound (IV) is defined by the structure of Compound (IV-D) and optionally salts and isomers thereof:

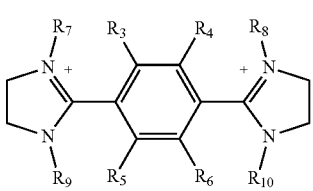

(IV-D)

In Compound (IV-D), $R_1$, $R_2$, $R_7$, and $R_8$ are each independently selected from —H, $C_1$-$C_{24}$ alkyl, $C_1$-$C_{24}$ aminoalkyl, $C_1$-$C_{24}$ alkanoalkyl, —P(OH)$O_2^-$, —$SO_3^-$ and $C_7$-$C_{20}$ arylalkyl such as benzyl group. In Compound (IV-D), $R_3$, $R_4$, $R_5$, $R_6$ are each independently selected from —H, —OH, $C_1$-$C_4$ alkyl, and $C_1$-$C_4$ alkylcarboxy. In Compound (IV-D), $R_9$ and $R_{10}$ are each independently selected from —$CH_2CH_2NHCH_2CH(OH)CH_2OC(O)R_1$, —$CH_2CH_2NHCH_2CH(OH)CH_2OC(O)R_2$, —$CH_2CH_2OCH_2CH(OH)CH_2OC(O)R_1$, and —$CH_2CH_2OCH_2CH(OH)CH_2OC(O)R_2$.

In some implementations, Compound (IV-D) is defined by the structures of Compounds (IV-D-1) and (IV-D-2):

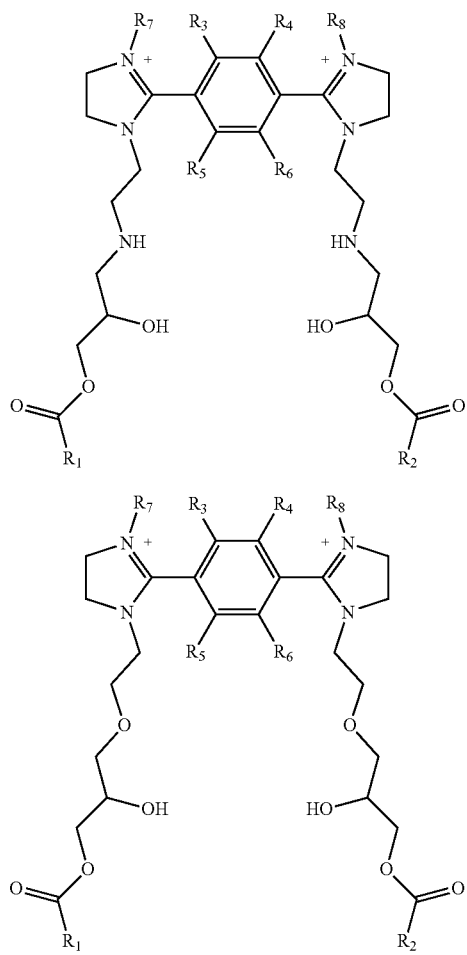

(IV-D-1)

(IV-D-2)

In Compounds (IV-D-1) and (IV-D-2), $R_1$, $R_2$, $R_7$, and $R_8$ are each independently selected from H, $C_1$-$C_{24}$ alkyl, $C_1$-$C_{24}$ aminoalkyl, $C_1$-$C_{24}$ alkanoalkyl, —P(OH)$O_2^-$, —$SO_3^-$ and $C_7$-$C_{20}$ arylalkyl such as benzyl group In Compounds (IV-D-1) and (IV-D-2), $R_3$, $R_4$, $R_5$, $R_6$ are each independently selected from —H, —OH, $C_1$-$C_4$ alkyl, and $C_1$-$C_4$ alkylcarboxy.

In some implementations, Compound (IV) is defined by the structure of Compound (IV-E) and optionally salts and isomers thereof:

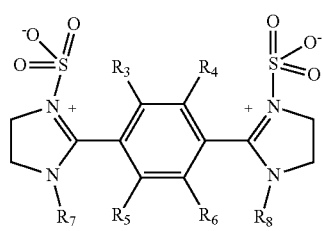

(IV-E)

In Compound (IV-E), $R_1$ and $R_2$ are each independently selected from H, $C_1$-$C_{24}$ alkyl, $C_1$-$C_{24}$ aminoalkyl, and $C_1$-$C_{24}$ alkanoalkyl. In Compound (IV-E), $R_3$, $R_4$, $R_5$, $R_6$ are each independently selected from —H, —OH, $C_1$-$C_4$ alkyl, and $C_1$-$C_4$ alkylcarboxy. In Compound (IV-E), $R_7$ and $R_8$ are each independently selected from —$CH_2CH_2NHR_1$, —$CH_2CH_2NHR_2$, —$CH_2CH_2NHC(O)R_1$, —$CH_2CH_2NHC(O)R_2$, —$CH_2CH_2OR_1$, —$CH_2CH_2OR_2$, —$CH_2CH_2OC(O)R_1$, and —$CH_2CH_2OC(O)R_2$.

In some implementations, Compound (IV-E) is defined by the structure of Compounds (IV-E-1), (IV-E-2), (IV-E-3), (IV-E-4), (IV-E-5) and (IV-E-6) and optionally salts and isomers thereof:

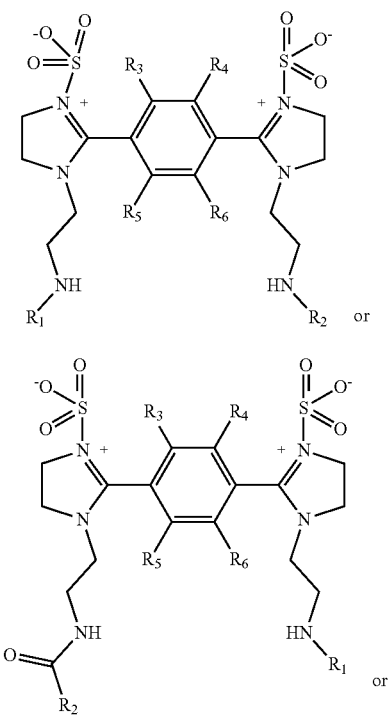

(IV-E-1)

(IV-E-2)

(IV-E-3)

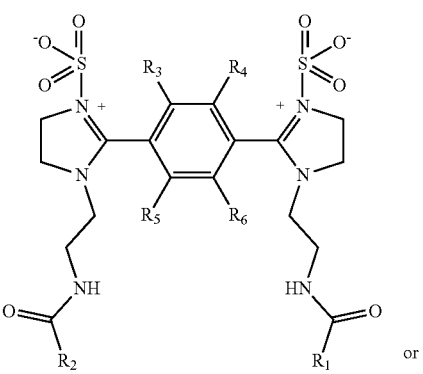

(IV-E-4)

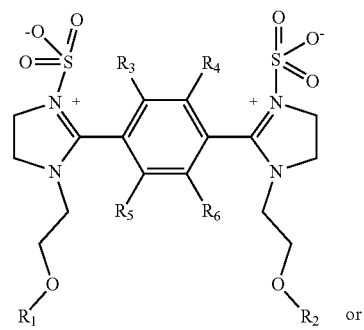

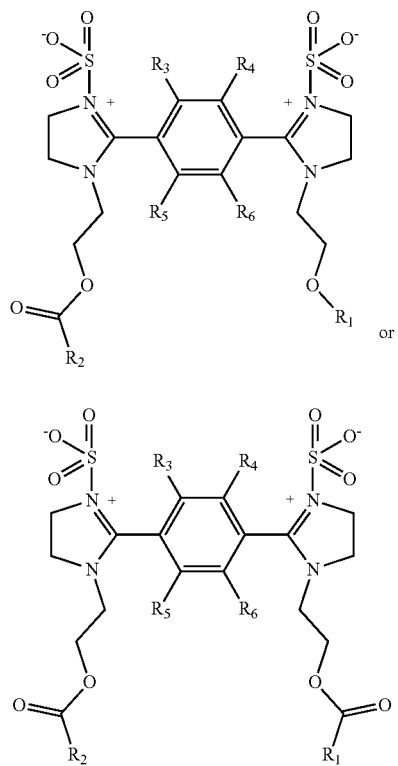

(IV-E-5)

(IV-E-6)

In Compounds (IV-E-1), (IV-E-2), (IV-E-3), (IV-E-4), (IV-E-5) and (IV-E-6), $R_1$ and $R_2$ are each independently selected from $C_1$-$C_{24}$ alkyl, $C_1$-$C_{24}$ aminoalkyl, and $C_1$-$C_{24}$ alkanoalkyl. In Compounds (IV-E-1), (IV-E-2), (IV-E-4), (IV-E-5) and (IV-E-6), $R_3$, $R_4$, $R_5$, $R_6$ are each independently selected from —OH, $C_1$-$C_4$ alkyl, and $C_1$-$C_4$ alkylcarboxy.

In some implementations, Compound (IV) is defined by the structure of Compound (IV-F):

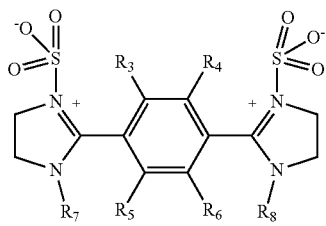

(IV-F)

In Compound (IV-F), $R_1$ and $R_2$ are each independently selected from —H, $C_1$-$C_{24}$ alkyl, $C_1$-$C_{24}$ aminoalkyl, and $C_1$-$C_{24}$ alkanoalkyl. In Compound (IV-F), $R_3$, $R_4$, $R_5$, $R_6$ are each independently selected from —H, $C_1$-$C_4$ alkyl, and $C_1$-$C_4$ alkylcarboxy. In Compound (IV-F), $R_7$ and $R_8$ are each independently selected from —CH$_2$CH$_2$NHCH$_2$CH(OH)CH$_2$OC(O)R$_1$, —CH$_2$CH$_2$NHCH$_2$CH(OH)CH$_2$OC(O)R$_2$, —CH$_2$CH$_2$OCH$_2$CH(OH)CH$_2$OC(O)R$_1$, and —CH$_2$CH$_2$OCH$_2$CH(OH)CH$_2$OC(O)R$_2$.

In some implementations, Compound (IV-F) is defined by the structures of Compounds (IV-F-1) and (IV-F-2):

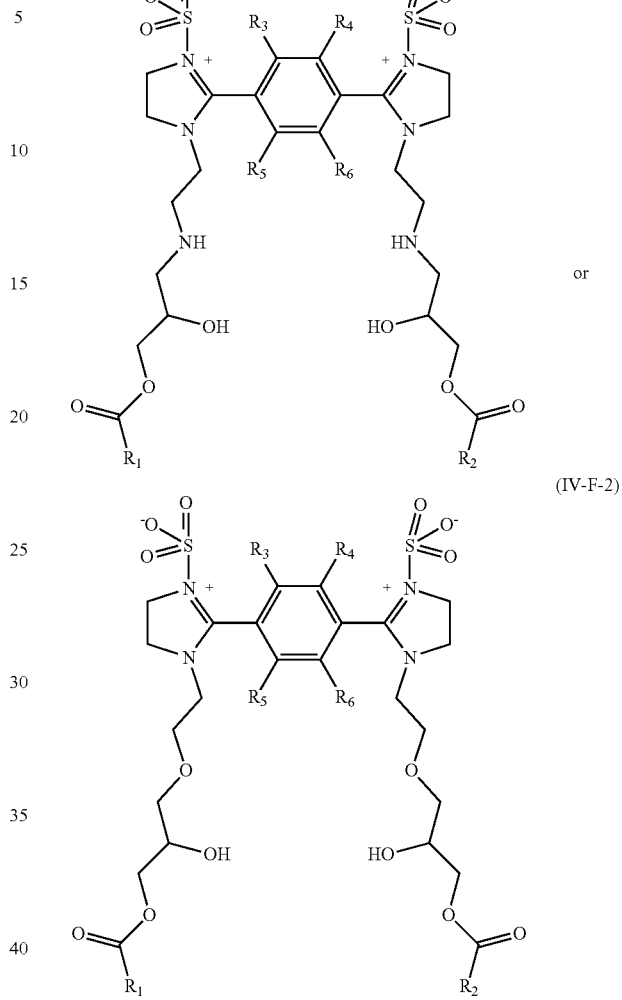

(IV-F-1)

(IV-F-2)

In Compounds (IV-F-1) and (IV-F-2), $R_1$ and $R_2$ are each independently selected from —H, $C_1$-$C_{24}$ alkyl, $C_1$-$C_{24}$ aminoalkyl, and $C_1$-$C_{24}$ alkanoalkyl. In Compounds (IV-F-1) and (IV-F-2), $R_3$, $R_4$, $R_5$, $R_6$ are each independently selected from —H, —OH, $C_1$-$C_4$ alkyl, and $C_1$-$C_4$ alkylcarboxy.

In some implementations, the composition of the present disclosure comprises the structure of Compound (V):

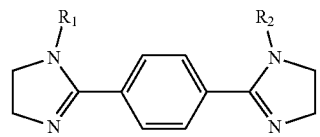

(V)

In Compound (V), $R_1$ and $R_2$ are each independently selected from —H, $C_1$-$C_{24}$ alkyl, $C_1$-$C_{24}$ aminoalkyl, $C_1$-$C_{24}$ alkanoalkyl, and —CH$_2$CH$_2$NHR$_3$. In Compound (V), $R_3$ is selected from the group of: —H, —C(O)C(R$_4$R$_5$R$_6$), —CH$_2$CH(OH)CH$_2$OC(O)C(R$_4$R$_5$R$_6$). In Compound (V), $R_4$, $R_5$ and $R_6$ are each independently selected from $C_3$-$C_{19}$, —C(O)C(CH$_3$)R$_7$, and —C(O)R$_7$. In Compound (V), $R_7$ is a $C_3$-$C_{19}$ arylalkyl.

In some implementations, Compound (V) is defined by the structures of Compounds (V-A), (V-B), (V-C) and (V-D):

The composition may further comprise additional additives to, for example, facilitate handling, enhance solubility

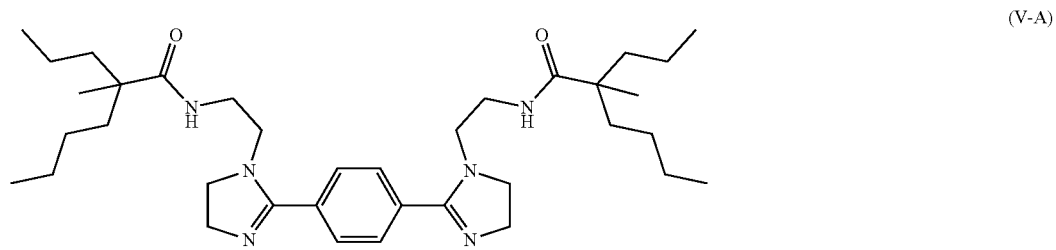
(V-A)

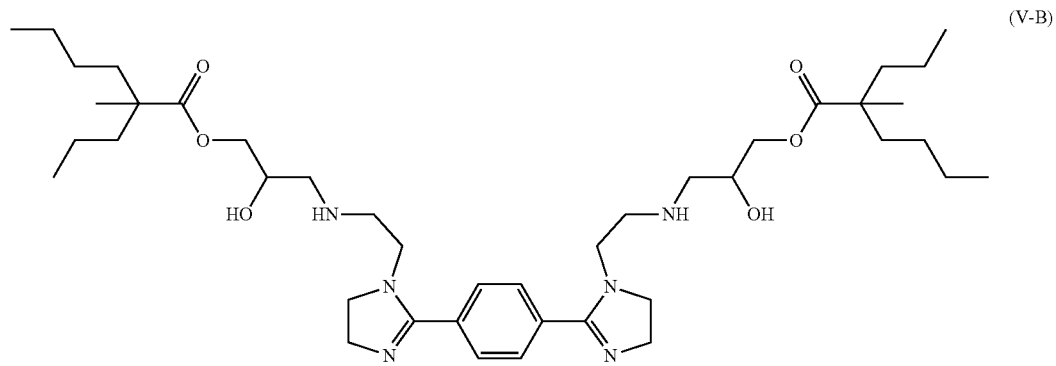
(V-B)

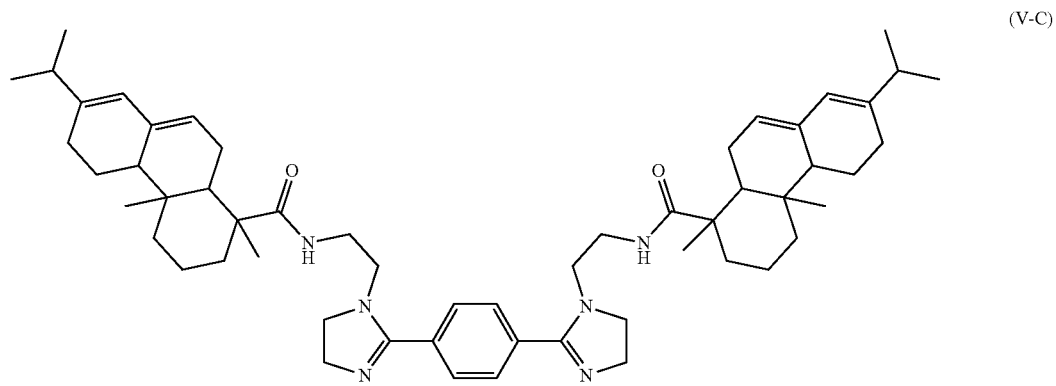
(V-C)

(V-D)

In some implementations, the composition of the present disclosure comprises the structure of Compound (VI) (and isomers thereof):

of the composition, and avoid operational problems such as foaming and the like. Examples of additives that may be used in the compositions of the present disclosure include,

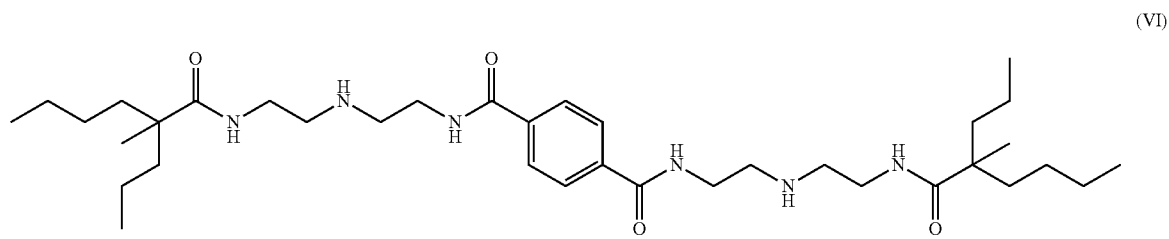 [SMILES: CCCCC(C)(CCC)C(=O)NCCNCCNC(=O)c1ccc(C(=O)NCCNCCNC(=O)C(C)(CCC)CCCC)cc1]
(VI)

but are not limited to, at least one of: surfactants, acids, film forming agents, solvents and/or freeze point depressors, scale inhibitors, wetting agents, and alkylene oxides.

In some implementations, the composition further comprises a surfactant. Suitable surfactants that may be used in the compositions of the present disclosure include surface active additives that may be used to formulate antifouling additives, corrosion inhibitors, anti-agglomeration agents, scale inhibitors, and other flow assurance related applications. Suitable surfactants also include surface-active additives that stabilize emulsion systems. The surfactants may help disperse the composition into the stream to be treated.

Suitable surfactants include, but are not necessarily limited to, non-ionic surfactants, anionic surfactants, quaternary ammonium compounds, and cationic surfactants. Examples of surfactants that may be used in the compositions of the present disclosure include, but are not necessarily limited to, alkoxylated alkyl alcohols and salts thereof and alkoxylated alkyl phenols and salts thereof, alkyl and aryl sulfonates, sulfates, phosphates, carboxylates, polyoxyalkyl glycols, fatty alcohols, polyoxyethylene glycol sorbitan alkyl esters, sorbitan alkyl esters, polysorbates, glucosides, tall oil, dimer/trimer acids, the products of maleated tall oil fatty acids, diethylene glycol ester and their salts, and the like, and combinations thereof. Other suitable surfactants include, but are not necessarily limited to, quaternary amine compounds, quaternary ammonium compounds, amine oxide surfactants, silicone based surfactants, and the like. These surfactants can be ionic, such as cationic surfactants such as quaternary alkyl amines or salts such as tetrabutylammomium acetate, tetrabutylammonium bromide, tetrabutylammonium nitrate, etc.; anionic surfactants such as sodium lauryl sulfate, sodium lauryl ether sulfate or dodecylbenzenesulfonic acid; or non-ionic surfactants such as polymers or copolymers based on ethylene oxide and propylene oxide and alkoxylates based on substrates such as alkylphenol or alkylphenol based resins, polyamines, nonylphenol ethoxylate, other polyols, or mixtures thereof. Exemplary quaternary ammonium based surfactants include alkyl dimethyl benzyl ammonium chloride, dialkyl dimethyl ammonium chloride, didecyl dimethyl ammonium chloride, alkyl dimethyl ethyl benzyl ammonium chloride, or mixtures thereof. The surfactant families can also include members from the amphoteric class, such as amine oxides, betaines, etc. Commercially available examples of surfactants that may be used with the compositions of the present disclosure include TERGITOL™ NP-9 Surfactant, TERGITOL™ NP-10 Surfactant, TERGITOL™ NP-15 Surfactant, TEGOSTAB® silicone surfactants, TENAX® WS-5520, and TENAX® WS-5560.

The at least one surfactant may be present in the composition in an amount greater than about 1% by weight; greater than about 5% by weight; greater than about 10% by weight; greater than about 20% by weight; greater than about 25% by weight; greater than about 30% by weight; greater than about 35% by weight; greater than about 40% by weight; greater than about 45% by weight; greater than about 50% by weight; greater than about 55% by weight; greater than about 60% by weight; greater than about 65% by weight; greater than about 70% by weight; greater than about 75% by weight; greater than about 80% by weight; greater than about 85% by weight relative to the total weight of the composition. The at least one surfactant may be present in the composition in an amount less than about 90% by weight; less than about 85% by weight; less than about 80% by weight; less than about 75% by weight; less than about 70% by weight; less than about 65% by weight; less than about 60% by weight; less than about 55% by weight; less than about 50% by weight; less than about 45% by weight; less than about 40% by weight; less than about 35% by weight; less than about 30% by weight; less than about 25% by weight; less than about 20% by weight; less than about 15% by weight; less than about 10% by weight relative to the total weight of the composition. The at least one surfactant may be present in the composition in an amount between about 1% by weight and about 90% by weight; between about 30% by weight and about 70% by weight; between about 40% by weight and about 60% by weight; between about 45% by weight and about 55% by weight, based on the total weight of the composition.

In some implementations, the composition further comprises an acid. Suitable acids include organic acids and inorganic acids that improve water solubility or oil solubility depending upon the application. Suitable inorganic acids include hydrochloric acid. Suitable organic acids include, but are not limited to, acetic acid, dimerized fatty acids (dicarboxylic acids prepared by dimerizing unsaturated fatty acids obtained from tall oil), trimerized fatty acids, phthalic acid, isophthalic acid, terephthalic acid, trimellitic acid, tetrahydrophthalic acid, hexahydrophthalic acid, tetrachlorophthalic acid, oxalic acid, adipic acid, azelaic acid, sebacic acid, succinic acid, malic acid, glutaric acid, malonic acid, pimelic acid, suberic acid, 2,2-dimethylsuccinic acid, 3,3-dimethylglutaric acid, 2,2-dimethylglutaric acid, maleic acid, fumaric acid, itaconic acid, fatty acids (linolic, oleic and the like), or mixtures thereof.

The at least one acid may be present in an effective amount for improving solubility of the composition. The at least one acid may be present in the composition in an amount greater than about 0.001% by weight; greater than about 0.01% by weight; greater than about 5% by weight; greater than about 10% by weight; greater than about 15% by weight; greater than about 20% by weight; greater than about 25% by weight relative to the total weight of the composition. The at least one acid may be present in the composition in an amount less than about 30% by weight; less than about 25% by weight; less than about 20% by weight; less than about 15% by weight; less than about 10% by weight; less than about 5% by weight, relative to the total weight of the composition. The at least one acid may be present in the composition in an amount between about 5% by weight and about 30% by weight; between about 10% by weight and about 25% by weight; between about 15% by weight and about 20% by weight based on the total weight of the composition.

In some implementations, the composition further comprises a solvent and/or freeze point depressors. Suitable solvents include solvents that will decrease the freezing point of the composition. Suitable solvents that may be used in the compositions of the present disclosure include, but are not necessarily limited to, formamide, propylene carbonate, tetrahydrofuran, alcohols, glycols, methanol, isopropanol, ethanol, acetone, toluene, xylene, monobutyl ether, dimethoxyethane, diglyme, naphtha, aprotic solvents such as dimethyl amine and n-methyl pyrrolidone or biodegradable or renewable solvents, and mixtures thereof alone or without water. Suitable glycols include ethylene glycol and propylene glycol. Suitable alcohols include methanol, ethanol, propanol, ethylene glycol, propylene glycol, and the like can also be used. Commercially available examples of solvents that may be used with the compositions of the present disclosure include Solvesso™ 150 Fluid and Augeo™ SL-191.

The at least one solvent and/or freeze point depressor may be present in the composition in an amount greater than about 10% by weight; greater than about 20% by weight; greater than about 25% by weight; greater than about 30% by weight; greater than about 35% by weight; greater than about 40% by weight; greater than about 45% by weight; greater than about 50% by weight; greater than about 55% by weight; greater than about 60% by weight; greater than about 65% by weight; greater than about 70% by weight; greater than about 75% by weight relative to the total weight of the composition. The at least one solvent may be present in the composition in an amount less than about 80% by weight; less than about 75% by weight; less than about 70% by weight; less than about 65% by weight; less than about 60% by weight; less than about 55% by weight; less than about 50% by weight; less than about 45% by weight; less than about 40% by weight; less than about 35% by weight; less than about 30% by weight; less than about 25% by weight; less than about 20% by weight; less than about 15% by weight relative to the total weight of the composition. The at least one solvent may be present in the composition in an amount between about 10% by weight and about 80% by weight; between about 20% by weight and about 70% by weight; between about 30% by weight and about 50% by weight, based on the total weight of the composition.

In some implementations, the composition further comprises a scale inhibitor. Scale inhibitors are added to produced waters from oil fields and gas fields to mitigate precipitation of minerals, especially sparingly soluble salts, present in the produced water that would occur during production and downstream processing of the water. Generally, the compounds subject to producing scale are referenced as scale formers. Those compounds include but are not limited to hardness, metals, alkalinity (including but not limited to carbonates), sulfates, silica, and combinations thereof. Such precipitation (scaling) leads to fouling and plugging of piping, valves, process equipment, and the oil-bearing formation. Suitable scale inhibitors that may be used in the compositions of the present disclosure include, but are not necessarily limited to, organophosphates, polyacrylic acid, polymaleic acid, hydrolyzed water-soluble copolymers of maleic anhydride, polycarboxylates, phosphonates, phosphates, sulfonates, polysulfonates, polycarboxylates, polyacrylates, and polyamides, along with the use of polyaspartic acids, and their mixtures with surfactants and emulsifiers for inhibiting or delaying precipitation of scale forming compounds. Other suitable scale inhibitors include, but are not necessarily limited to, phosphate esters, acetylenic alcohols, fatty acids and/or alkyl-substituted carboxylic acids and anhydrides, polyacrylic acids, quaternary amines, sulfur-oxygen phosphates, and/or polyphosphate esters.

The at least one scale inhibitor may be present in an effective amount for mitigating precipitation of minerals occurring during production. The at least one scale inhibitor may be present in the composition in an amount greater than about 0.1% by weight; greater than about 1% by weight; greater than about 2% by weight; greater than about 5% by weight; greater than about 10% by weight; greater than about 15% by weight, relative to the total weight of the composition. The at least one scale inhibitor may be present in the composition in an amount less than about 20% by weight; less than about 15% by weight; less than about 10% by weight; less than about 5% by weight; less than about 2% by weight; less than about 1% by weight, relative to the total weight of the composition. The at least one scale inhibitor may be present in the composition in an amount between about 1% by weight and about 20% by weight; between about 5% by weight and about 15% by weight; between about 5% by weight and about 10% by weight; between about 10% by weight and about 15% by weight, based on the total weight of the composition.

In some implementations, the composition further comprises a wetting agent. Suitable wetting agents in the compositions of the present disclosure include, but are not necessarily limited to, include glycols, silanes, anionic surfactants, cationic surfactants, non-ionic surfactants, and any other wetting agents known in the art. In one implementation, the wetting agent is an anionic surfactant, for example, sodium dioctyl sulfosuccinate.

The at least one wetting agent may be present in an effective amount for lowering the surface tension of the composition. The at least one wetting agent may be present in the composition in an amount greater than about 0.001% by weight; greater than about 0.01% by weight; greater than about 0.1% by weight; greater than about 1% by weight; greater than about 2% by weight; greater than about 5% by weight; greater than about 10% by weight; greater than about 15% by weight, relative to the total weight of the composition. The at least one wetting agent may be present in the composition in an amount less than about 20% by weight; less than about 15% by weight; less than about 10% by weight; less than about 5% by weight; less than about 2% by weight; less than about 1% by weight, relative to the total weight of the composition. The at least one wetting agent may be present in the composition in an amount between about 0.001% by weight and about 20% by weight; between about 0.01% by weight and about 10% by weight; between about 0.1% by weight and about 1% by weight, based on the total weight of the composition.

In some implementations, the composition further comprises an alkylene oxide. For example, each of aforementioned general structures containing a primary or secondary amine or hydroxyl functionality can also be subsequently reacted with one or more moles of an alkylene oxide as random or block-copolymers in any ratio or configuration to adjust solubility or optimize chemical performance. The alkylene oxide may be selected from ethylene oxide (EO), propylene oxide (PO) or butylene oxides (BO).

It should be understood that the compositions described herein may also include amid intermediates to the imidazolines, especially since the manufactured products may contain unconverted amid and the degree of conversion is a variable that may be adjusted for performance of the implementations described herein. Other amines and fatty acids, monoacids, diacids or higher acids and their derivatives can also be used to produce the chemical compounds of this disclosure according to the molecular structures described herein.

It is also important to note that the imidazoline function, as indicated in the molecular structures described herein, can exist at any position along the polyethyleneamine chain and is not limited to the positions indicated in the structures above. It is also possible that more than one bisimidazoline link can exist between the same two polyethyleneamine molecules, or even several links with several polyethyleneamine molecules.

It should be further understood that the respective amounts of the aforementioned components and any optional components used in the detectable composition will total 100 weight percent and amounts of the above stated ranges will be adjusted if necessary to achieve the same. In another implementation, the methods described herein can use the same composition amounts described above for the composition.

In one implementation, the composition comprises the reaction products of at least one of: (a) terephthalic acid, (b) a neo-acid having the structure $(R_1R_2R_3)$—C—COOH, wherein $R_1$, $R_2$ and $R_3$ are each independently selected from linear or branched alkyl groups, the neo-acid may be a $C_5$-$C_{22}$ neoacid, such as a such as a $C_5$-$C_{19}$ neoacid, for example, a $C_5$-$C_{10}$ neoacid, with $R_1+R_2+R_3$ having a combined 3 to 20 carbon atoms for a $C_5$-$C_{22}$ neoacid, $R_1+R_2+R_3$ having a combined 3 to 17 carbon atoms $C_5$-$C_{19}$ neoacid, $R_1+R_2+R_3$ having a combined 3 to 8 carbon atoms and $C_5$-$C_{10}$ neoacid, (c) acrylic acid, (d) diethylenetriamine, (e) rosin, (f) tall oil fatty acids, $C_{12}$-$C_{24}$ fatty acids, and other fatty acids, and (g) a glycidyl ester of a neo-acid. In one implementation, a mixture of one or more $C_5$-$C_{22}$ neo-acids, for example, a mixture of $C_{10}$-$C_{19}$ neo-acids or a mixture of $C_9$-$C_{13}$ neo-acids, may be used for the $C_5$-$C_{22}$ neo-acid described herein.

Suitable neo-acids that may be used to form the compositions described herein include $C_5$-$C_{19}$ neo-acids having the structure $(R_1R_2R_3)$—C—COOH, wherein $R_1$, $R_2$ and $R_3$ are each independently, linear or branched alkyl groups having together a total of 3 to 17 carbon atoms (for example, 2, 3, 4, 5, 6, 7, 8, 9, 10, 11, 12, 13, 14, 15, 16 or 17 carbon atoms). In one implementation, at least one of $R_1$, $R_2$ and $R_3$ is a methyl group. In another implementation, at least two of $R_1$, $R_2$ and $R_3$ are methyl groups. In another implementation, $R_1$, $R_2$ and $R_3$ are methyl groups. Suitable neo-acids that may be used to form the compositions described herein include neo-pentanoic acid, neo-hexanoic acid, neo-heptanoic acid, neo-nonanoic acid, neo-decanoic acid, isomers thereof, and combinations thereof. Examples of commercially available neo-acids that may be used with the implementations described herein are available from HEXION™ under the tradename Versatic™ acid. Commercially available Versatic™ acids that may be used with the implementations described herein include Versatic™ Acid 10 and Versatic™ Acid 5.

Suitable glycidyl esters of neo-acids that may be used to form the compositions described herein have the structure:

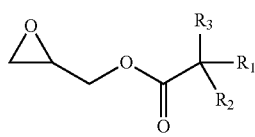

(VII)

wherein $R_1$, $R_2$ and $R_3$ are each independently linear or branched alkyl groups having together a total of 2 to 9 carbon atoms (for example, 2, 3, 4, 5, 6, 7, 8 or 9 carbon atoms). In one implementation, $R_3$ is a methyl group and $R_1$ and $R_2$ together have a total of seven carbon atoms. Examples of commercially available glycidyl esters of neo-acids that may be used with the implementations described herein are available from HEXION™ under the name Cardura™ Glycidyl Ester E10P (a glycidyl ester of Versatic™ acid 10).

EXAMPLES

Aspects and advantages of the implementations described herein are further illustrated by the following examples. The particular materials and amounts thereof, as well as other conditions and details, recited in these examples should not be used to limit the implementations described herein. All parts and percentages are by weight unless otherwise indicated.

A description of raw materials used in the examples as follows.

| | |
|---|---|
| Acrylic Acid | Available from Sigma-Aldrich ®. |
| Aminoethylethanolamine | Available from Sigma-Aldrich ®. |
| Cardura ™ Glycidyl Ester E10P | A glycidal ester of Versatic ™ Acid 10, commercially available from HEXION ™. |
| Diethylenetriamine | Available from Sigma-Aldrich ®. |
| MWV ® Rosin-S | Available from Ingevity. |
| Propylene glycol | Available from Sigma-Aldrich ®. |
| Terephthalic acid | Available from Sigma-Aldrich ®. |
| Versatic ™ Acid 10 | A synthetic, highly branched C-10 tertiary carboxylic acid, commercially available from HEXION ™. Also known as neo-decanoic acid. |

Procedure for the Synthesis of Compound (V-D):

Diethylenetriamine (206.0 g, 2.0 mol) was charged to a 500 ml round bottom flask equipped with an over-head agitator. The flask was heated to 145 degrees Celsius with slow agitation. Terephthalic acid (166.3 g, 1.0 mol) was charged to the flask in several portions at a rate such that no clumping of large mass was formed. The mixture was then heated to 170-190 degrees Celsius, and maintained at this temperature for 2-3 hours, and about 35 ml water was collected. The resulting intermediate was further heated to 250-270 degrees Celsius, and maintained at this temperature for 4 hours. An additional 35 ml of water was collected. The reaction was cooled to room temperature to give Compound (V-D) (295.0 g, quantitative).

Procedure for the Synthesis of Compound (V-A):

Versatic™ acid (32.8 g, 130.6 mmol) was added to Compound (V-D) (19.6 g, 65.3 mmol) in a round bottom flask. The mixture was heated to 170-190 degrees Celsius and maintained at this temperature for 4 hours. Then the reaction was heated to 210 degrees Celsius and maintained at this temperature for 1 hour. Unreacted Versatic™ acid, water and other volatile by-products were distilled, providing a brown, transparent liquid, Compound (V-A), which solidified at 60 degrees Celsius. Fourier Transform Infrared Spectroscopy (FTIR) showed the disappearance of the carboxy group.

Procedure for the Synthesis of Compound (V-B):

Cardura™ E10P monomer (13.0 g, 5.6 mmol) was added dropwise to Compound (V-D) (8.6 g, 2.8 mmol) in a round bottom flask heated at 100 degrees Celsius. The reaction did not start until the temperature was raised to 120 degrees Celsius. The mixture eventually became homogeneous. The reaction was allowed to run 1.5 hours at 130 degrees Celsius to give Compound (V-B) as a viscous brown liquid. FTIR showed the disappearance of the epoxy group.

Procedure for the Synthesis of Compound (V-C):

S-Rosin (35.0 g, 116 mmol) and Compound (V-D) (17.4 g, 58.0 mmol) were combined, and heated to 130 degrees Celsius. The reactants formed a slurry that slowly melted when the mixture was further heated up to 190-210 degrees Celsius. The reaction was maintained at this temperature for 3 hours, or until no further water formation, to give Compound (V-C) as a brown liquid, which solidified at RT.

Procedure for the Synthesis of Compound (VI):

Terephthalic acid (8.3 g, 50 mmol) was charged to a round bottom flask with diethylenetriamine (20.6 g, 200 mmol). The mixture was heated to 140 degrees Celsius, and the mixture melted. The other portion of terephthalic acid (8.3 g, 50 mmol) was charged to the flask, and the mixture was heated to 210-220 degrees Celsius, and held at this temperature for 2 hours. After 3.5 ml of water was collected, the reaction was stopped to give Compound (VI) as a yellow liquid which solidified at RT. FTIR showed the disappearance of the carboxy group.

Procedure for the Synthesis of Compound (IV-B-5):

Compound (V-A) (13.7 g, 22.5 mmol) was dissolved in propylene glycol (15.0 g) at 100 degrees Celsius. The solution was cooled to 90 degrees Celsius, and acrylic acid (3.25 g, 45.0 mmol) was added to the solution dropwise. The reaction was heated to 100 degrees Celsius and maintained at this temperature for 1.5 hours. Then the temperature was raised to 120 degrees Celsius, and maintained at the temperature for 1.5 hours to give Compound (IV-B-5) as a brown liquid. FTIR indicated the disappearance of the carbon-carbon double bond.

Procedure for the Synthesis of Compound (I-I):

Step 1:

Versatic™ acid (17.2 g, 100 mmol) was added dropwise to a round bottom flask containing diethylenetriamine (12.4 g, 120 mmol). The resulting mixture was heated to 170-190 degrees Celsius and maintained at this temperature for 6 hours. FTIR indicated the disappearance of carboxy group. The reaction was further heated to 250-260 degrees Celsius, and maintained at this temperature for 2 hours until no further distillates were coming out to give the Versatic™ acid imidazoline intermediate as a viscous liquid which solidified at room temperature. FTIR indicated the appearance of imidazolinyl group.

Step 2:

9.51 g of the intermediate (39.8 mmol) from Step 1 was dissolved in 12 g of propylene glycol at 80 degrees Celsius to form a solution. To the solution was added acrylic acid (2.87 g, 39.8 mmol) dropwise. The reaction was held at 80 degrees Celsius for 1 hour. Then the temperature was raised to 100 degrees Celsius, and maintained at 100 degrees Celsius for 1.5 hours. The reaction was further heated to 120 degrees Celsius, and maintained at 120 degrees Celsius for 1.5 hours to give Compound (I-I) as a dark viscous liquid.

Procedure for the synthesis of Compound (I-J)

Step 1:

Versatic™ acid (51.3 g, 300 mmol) was added dropwise to a round bottom flask with AEEA (aminoethylethanolamine) (31.2 g, 300 mmol) heated at 80 degrees Celsius. After the addition was complete, the reaction was heated to 210-230 degrees Celsius for 3 hours, and about 7 ml of distillates was collected. The reaction was further heated to 275 degrees Celsius, and held for 2 hours, and 3 ml of additional distillates was collected. The reaction was cooled to 80 degrees Celsius, and acrylic acid (21.6 g, 300 mmol) was added dropwise. After the addition was complete, the reaction was heated up to 100 degrees Celsius, and maintained at 100 degrees Celsius for 2 hours. The reaction was further heated to 120 degrees Celsius, and maintained for 2 hours to give Compound (I-J) as a viscous dark liquid.

Test Methods

Two test methods were developed and used to evaluate the effect of the experimental products on the fouling behavior of fluid obtained from a SAGD facility. The first test method included a stainless steel coupon that was partially submersed into a glass container equipped with a magnetic stirrer positioned directly below the coupon. The glass container contained a fixed batch of process water obtained from a SAGD operating plant.

Figure 2:
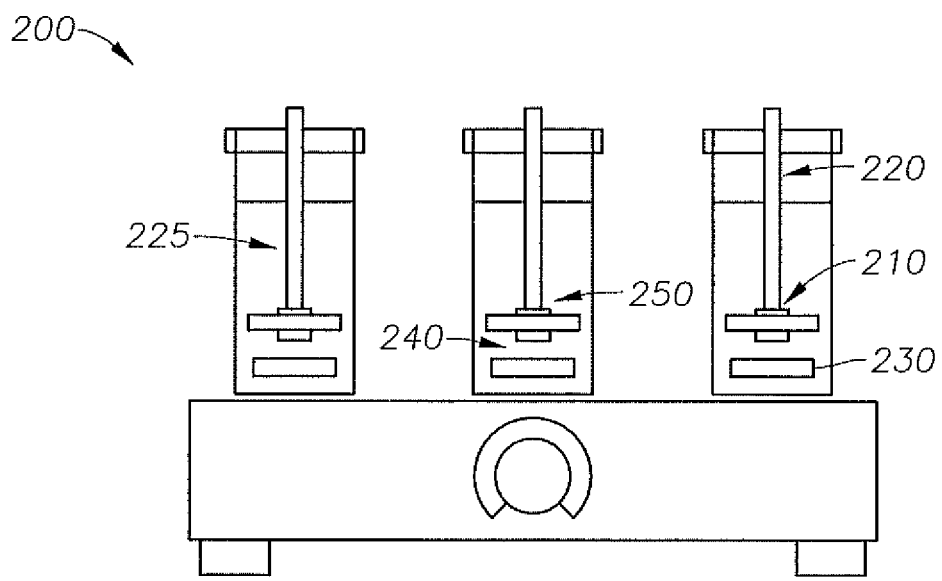
FIG. 2 is a schematic of an experimental test set-up for testing the compositions according to one implementation of the present disclosure.

FIG. 2 is a schematic diagram of the experimental test set-up 200 for the second test method. The second test method was similar, but the coupon was replaced with a stainless steel washer 210 on a stainless steel bolt 220 held in position by a stainless steel nut and placed in the SAGD produced fluid 225. The magnetic stirrer 230 was positioned directly below the horizontal washer, creating a high shear condition 240 at the bottom of the washer and a reduced shear rate 250 at the top of the washer. A nine-place magnetic stirrer plate was used in both test methods to ensure identical agitation in each test container for each set of experiments. Chemical performance was determined by evaluating the amount of deposited material as a function of time and chemical concentration.

It is important to note that this test method allows simultaneous performance evaluation under low as well as high shear conditions. In addition to the shear condition, the coupon described also introduce several different surfaces, such as the machined thread on the shaft and the tight gap between the nut and the washer, all conditions relevant to the anti-fouling performance test.

Results

Figure 3:
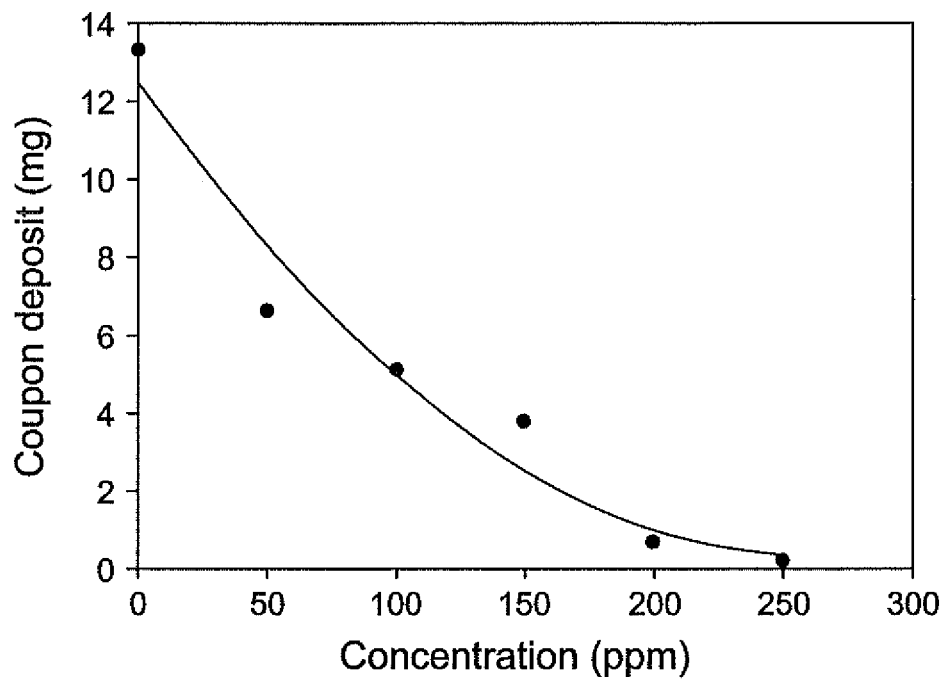
FIG. 3 is a plot of mass of deposit recorded as a function of anti-fouling concentration for a composition containing Compound No. (I-I)

FIG. 3 shows a graph of mass of deposit recorded as a function of anti-fouling concentration for a formula containing Compound (I-H). Stainless steel coupons were exposed to SAGD fluid treated with Compound (I-H) at increasing concentrations for a period of four hours of stirring at 200 RPM at room temperature. The data is a reflection of the average deposit, including both conditions; high and low shear. It was noted that approximately 50% reduction in deposit amount is achieved at an anti-fouling concentration of 50 ppm.

Figure 4:
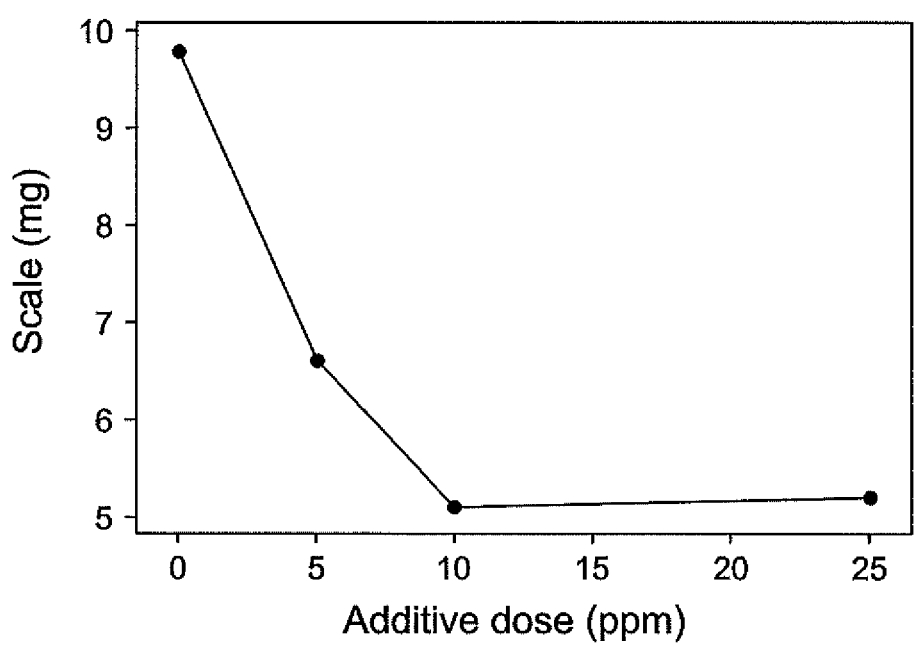
FIG. 4 is a plot of mass of deposit recorded as a function of anti-fouling concentration for a composition containing Compound No. (V-B).

FIG. 4 shows a graph of mass of deposit recorded as a function of anti-fouling concentration for a formula containing Compound (VII) for a calcium-scaling test. The results are depicted in Table I.

TABLE I

| Dose, ppm | Deposit, mg |
|---|---|
| 25 | 5.2 |
| 10 | 5.1 |
| 5 | 6.6 |
| 0 | 9.8 |

As depicted in FIG. 3 and FIG. 4, the compositions of the present disclosure have demonstrated high effectiveness in reducing deposition of SAGD fluid on the metal surface in laboratory test.

Although the implementations described herein are typically used for passivation in SAGD systems, it should be understood that some implementations described herein are also applicable to other systems where passivation of metal surfaces, clay surfaces, or both are desirable.

While the foregoing is directed to implementations of the present disclosure, other and further implementations of the disclosure may be devised without departing from the basic scope thereof, and the scope thereof is determined by the claims that follow.

What is claimed is:

1. A composition, comprising:
at least one compound selected from the group consisting of Compounds (II) and (V):

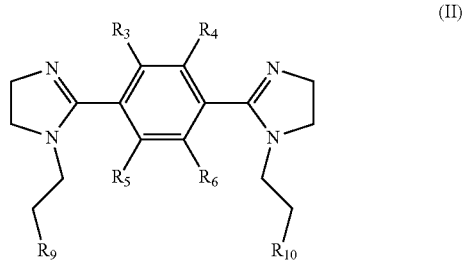

wherein for Compound (II), $R_3$, $R_4$, $R_5$, and $R_6$ are each independently selected from $C_1$-$C_4$ alkyl, and $C_1$-$C_4$ alkylcarboxy, and $R_9$ and $R_{10}$ are each independently selected from —$NHR_1$, —$NHR_2$, —$NHC(O)R_1$, and —$NHC(O)R_2$, wherein $R_1$ and $R_2$ are each independently $C_1$-$C_{36}$ alkylcarboxy;

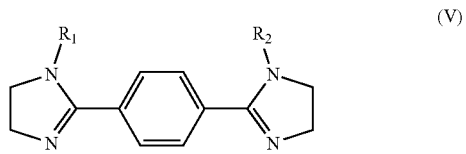

wherein for Compound (V), $R_1$ and $R_2$ are each independently —$CH_2CH_2NHR_3$, $R_3$ is selected from the group of: —$C(O)C(R_4R_5R_6)$, —$CH_2CH(OH)CH_2OC(O)C(R_4R_5R_6)$, $R_4$, $R_5$, and $R_6$ are each independently selected from $C_3$-$C_{19}$, —$C(O)C(CH_3)R_7$, and —$C(O)R_7$, and $R_7$ is a $C_3$-$C_{19}$ arylalkyl; and
optionally salts and isomers of Compounds (II-V), and combinations thereof.

2. The composition of claim 1, further comprising:
an additive selected from the group consisting of: surfactants, acids, film forming agents, solvents, freeze point depressors, scale inhibitors, wetting agents, and alkylene oxides.

3. The composition of claim 1, further comprising a scale inhibitor selected from the group consisting of: phosphate esters, acetylenic alcohols, fatty acids and/or alkyl-substituted carboxylic acids and anhydrides, quaternary amines, sulfur-oxygen phosphates and/or polyphosphate esters, and combinations thereof.

4. The composition of claim 1, further comprising a surfactant selected from the group consisting of: quaternary alkyl amines, tetrabutylammomium acetate, tetrabutylammonium bromide, tetrabutylammonium nitrate, sodium lauryl sulfate, sodium lauryl ether sulfate, polyamines, polymers or copolymers comprising ethylene oxide, propylene oxide, alkoxylates of alkylphenol or alkylphenol based resins, and combinations thereof.

5. The composition of claim 1, further comprising a solvent selected from the group consisting of: formamide, propylene carbonate, tetrahydrofuran, alcohols, glycols, methanol, isopropanol, ethanol, acetone, toluene, xylene, monobutyl ether, dimethoxyethane, diglyme, naphtha, dimethyl amine, n-methyl pyrrolidone, biodegradable solvents, or renewable solvents, and mixtures thereof, with or without water.

6. A method of treating fouling of a metallic component, the method comprising:
contacting a metallic component with the composition of claim 1; and
contacting the metallic component with a hydrocarbon-containing process fluid stream.

7. The method of claim 6, wherein contacting the metallic component comprises continuously injecting the composition into the hydrocarbon-containing process fluid stream during operation.

8. The method of claim 6, wherein the metallic component is a heat exchanger.

9. The method of claim 6, wherein the hydrocarbon-containing process fluid stream is a steam assisted oil recovery system.

10. The method of claim 7, wherein between about 1 ppm and about 1000 ppm of the composition is injected into the hydrocarbon-containing process fluid stream.

11. The method of claim 10, wherein between about 5 ppm and about 750 ppm of the composition is injected into the hydrocarbon-containing process fluid stream.

12. The composition of claim 1, wherein Compound (II) has the formula:

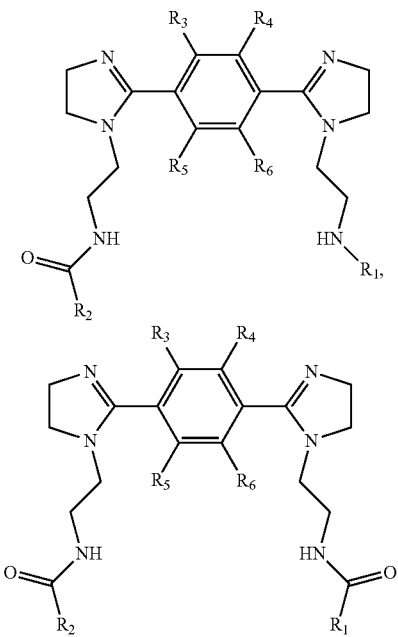

or combinations thereof,
wherein $R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy.

13. The composition of claim 12, wherein for Compound (II), $R_1$ and $R_2$ are each independently selected from —H, $C_1$-$C_{24}$ alkyl, and $C_1$-$C_{24}$ aminoalkyl.

14. The composition of claim 12, wherein for Compound (II), $R_1$ and $R_2$ are each independently selected from $C_1$-$C_{24}$ alkanoalkyl and $C_1$-$C_{36}$ alkylcarboxy.

15. A composition, comprising:
a surfactant,
a corrosion inhibitor;
a solvent; and at least one compound selected from the group consisting of:

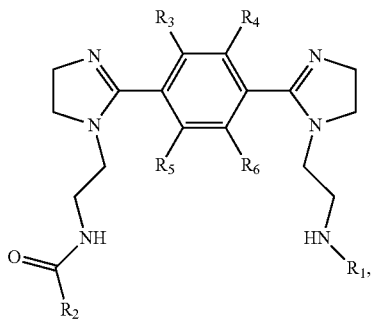

and optionally salts thereof,

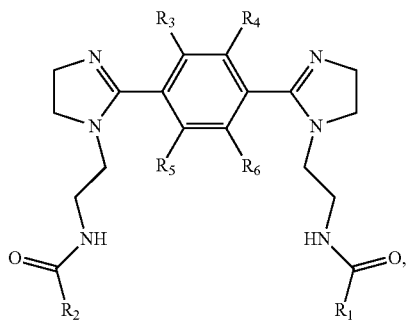

and optionally salts thereof, and combinations thereof, wherein:

$R_1$ and $R_2$ are each independently selected from —H, $C_1$-$C_{24}$ alkyl, $C_1$-$C_{24}$ aminoalkyl, $C_1$-$C_{24}$ alkanoalkyl, and $C_1$-$C_{36}$ alkylcarboxy, and $R_3$, $R_4$, $R_5$, and $R_6$ are each independently selected from —H, $C_1$-$C_4$ alkyl, and $C_1$-$C_4$ alkylcarboxy.

16. The composition of claim 15, further comprising a scale inhibitor selected from the group consisting of: phosphate esters, acetylenic alcohols, fatty acids and/or alkyl-substituted carboxylic acids and anhydrides, quaternary amities, sulfur-oxygen phosphates and/or polyphosphate esters, and combinations thereof.

17. The composition of claim 15, wherein the surfactant is selected from the group consisting of: quaternary alkyl amines, tetrabutylammomium acetate, tetrabutylammonium bromide, tetrabutylammonium nitrate, sodium lauryl sulfate, sodium lauryl ether sulfate, polyamines, polymers or copolymers comprising ethylene oxide, propylene oxide, alkoxylates of alkylphenol or alkylphenol based resins, and combinations thereof.

18. The composition of claim 15, wherein the solvent is selected from the group consisting of: formamide, propylene carbonate, tetrahydrofuran, alcohols, glycols, methanol, isopropanol, ethanol, acetone, toluene, xylene, monobutyl ether, dimethoxyethane, diglyme, naphtha, dimethyl amine, n-methyl pyrrolidone, biodegradable solvents, or renewable solvents, and mixtures thereof, with or without water.

* * * * *